United States Patent
Sinclair et al.

(10) Patent No.: US 12,252,505 B2
(45) Date of Patent: Mar. 18, 2025

(54) SIRT1 ACTIVATING COMPOUNDS

(71) Applicant: President and Fellows of Harvard College, Cambridge, MA (US)

(72) Inventors: David A. Sinclair, Chestnut Hill, MA (US); Conrad Rinaldi, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 771 days.

(21) Appl. No.: 17/284,691

(22) PCT Filed: Oct. 16, 2019

(86) PCT No.: PCT/US2019/056487
§ 371 (c)(1),
(2) Date: Apr. 12, 2021

(87) PCT Pub. No.: WO2020/081654
PCT Pub. Date: Apr. 23, 2020

(65) Prior Publication Data
US 2021/0371446 A1  Dec. 2, 2021

Related U.S. Application Data

(60) Provisional application No. 62/746,251, filed on Oct. 16, 2018.

(51) Int. Cl.
| | | |
|---|---|---|
| *C07H 19/048* | (2006.01) | |
| *A61K 45/06* | (2006.01) | |
| *C07D 213/80* | (2006.01) | |
| *C07D 213/82* | (2006.01) | |
| *C07D 401/12* | (2006.01) | |
| *C07D 401/14* | (2006.01) | |
| *C07D 409/12* | (2006.01) | |

(52) U.S. Cl.
CPC .......... *C07H 19/048* (2013.01); *A61K 45/06* (2013.01); *C07D 213/80* (2013.01); *C07D 213/82* (2013.01); *C07D 401/12* (2013.01); *C07D 401/14* (2013.01); *C07D 409/12* (2013.01)

(58) Field of Classification Search
CPC .. C07D 213/80; C07D 401/14; C07D 213/82; C07D 401/12; C07D 409/12; C07H 19/048; A61P 3/04; A61P 3/10; A61P 9/00; A61P 11/00; A61P 19/10; A61P 25/28; A61P 35/00; A61K 45/06
See application file for complete search history.

(56) References Cited

U.S. PATENT DOCUMENTS

2017/0267709 A1* 9/2017 Migaud ................ C07H 19/048

FOREIGN PATENT DOCUMENTS

| CN | 105853378 A | * 8/2016 | .......... A61K 31/455 |
|---|---|---|---|
| EP | 2774915 A1 | 9/2014 | |
| WO | WO-2005/069998 A2 | 8/2005 | |
| WO | WO-2006/134282 A1 | 12/2006 | |
| WO | WO-2007/005453 A2 | 1/2007 | |
| WO | WO-2017/013120 A1 | 1/2017 | |
| WO | WO-2017/096450 A1 | 6/2017 | |
| WO | WO-2017/161165 A1 | 9/2017 | |
| WO | WO-2018/164662 A1 | 9/2018 | |
| WO | WO-2020/081654 A1 | 4/2020 | |

OTHER PUBLICATIONS

Ngo et al., Phytochemistry, 1998, 47(6), p. 1117-1123. (Year: 1998).*
Belofsky et al., J. Nat. Prod., 2004, 67, p. 481-484. (Year: 2004).*
Orallo, F., Current Medicinal Chemistry, 2006, 13, p. 87-98. (Year: 2006).*
Bernini et al., "New lipophilic piceatannol derivatives echibiting antioxidant activity perpared by aromatic hydroxylation with 2-iodoxybenzoic acid (IBX)," Molecules, 14(12):4669-4681 (2009).
Cardile et al., "Chemo-enzymatic synthesis and cell-growth inhibition activity of reseratrol analogues," Bioorganic Chemistry, 33(1):22-33 (2005).
International Search Report and Written Opinion for International Application No. PCT/US2019/056487 dated Feb. 14, 2020.
Liu et al., "Synthesis and biological evaluation of resvertrol derivatives as melanogenesis inhibitors," Molecules online, 20(9):16933-16945 (2015).
Mattarei et al., "N-monosubstituted methoxy-oligo(ethylene glycol) carbamate ester prodrugs of resveratrol," Molecules Online, 20(9):16085-16102 (2015).
Oh et al., "Lipophilization of resveratrol and effects on antioxidant activities," Journal of Agricultural and food chemistry,: 65(39):8617-8625 (2017).
Pablo et al., "Alkylated reseratrol prodrugs and metabolites as potential therapeutics for neurodegenerative diseases," European Journal of Medicinal Chemistry, 146:123-138 (2018).

(Continued)

*Primary Examiner* — Jonathan S Lau
(74) *Attorney, Agent, or Firm* — Foley Hoag LLP; DeAnn F. Smith; David S. Surry

(57) ABSTRACT

Provided herein are methods and compositions for preventing or treating aging, or an aging-related disorder, a disorder associated with inflammation, or for modulating an immune response in a subject in need thereof. In some embodiments, the methods comprise administering to the subject an effective amount of a compound of Formulas I-XIII.

19 Claims, No Drawings

(56) References Cited

OTHER PUBLICATIONS

Peng et al., "Synthesis and biological evaluation of novel resveratrol—NSAID derivatives as anti-inflammatory agents," Chemical and Pharmaceutical Bulletin, 64(6):609-615 (2016).

Urbaniak et al., "Activity of resveratrol triesters against primary acute lymphoblastic leukemia cells," Bioorganic & Medicinal Chemistry Letters, 27(12):2766-2770 (2017).

Yang et al., "Synthesis and anticoagulant bioactivity of heterocyclic derivatives of resveratrol," Chemistry of Natural Compounds, 54(5):864-868 (2018).

Yuan et al., "Synthesis of pterostilbene and resveratrol carbamate derivitives as potential dual cholinesterase inhibitors and neuroprotective agents," Research on Chemical Intermediates, 787-800 (2013).

* cited by examiner

SIRT1 ACTIVATING COMPOUNDS

CROSS-REFERENCE TO RELATED APPLICATIONS

This application is a § 371 national-stage application based on PCT/US19/56487, filed Oct. 16, 2019 which claims the benefit of U.S. Provisional Application No. 62/746,251 filed on Oct. 16, 2018; the entire contents of said applications are incorporated herein in their entirety by this reference.

GOVERNMENT SUPPORT

This invention was made with government support under DK100263 and AG028730 awarded by the National Institutes of Health. The government has certain rights in this invention.

BACKGROUND

SIRT1 Activating Compounds, (STACs), e.g. (resveratrol, butein, piceatannol, fisetin and quercetin) are of interest in geriatric research and cosmetics due to their ability to improve the health of skin and alleviate a variety of age related diseases by activating SIRT1 protein, an NAD+-dependent protein deacylase. STACs, like resveratrol, acts as allosteric activators, which increase SIRT1 activity by raising the affinity for its substrate. However, SIRT1 activity is also dependent on its co-substrate NAD+. Endogenous levels of NAD+ decrease with age making STACS less effective in really old mammals. Pharmacologically raising NAD+ levels in vivo using NAD Precursors (NPs) has been proven to be effective in boosting SIRT1 activity and alleviate various symptoms of aging and age-related diseases. However, low stability and inconsistent pharmacokinetics have impeded their translation into an effective drug like molecules. Therefore, development of a new class of SIRT1 activators is imperative to get full benefits of SIRT1 activation during aging. Thus, there is a need for novel compounds to improve the stability and pharmacokinetics of STACS for therapeutic uses.

SUMMARY

In one aspect, provided herein are compounds having a structure of Formula I, II, II, IV, V, VI, VII, VIII, IX, X, or XI, or a pharmaceutically acceptable salt thereof:

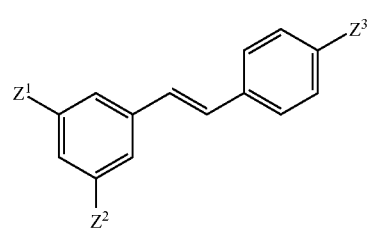

I

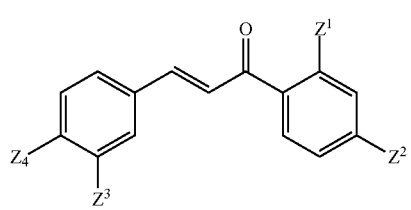

II

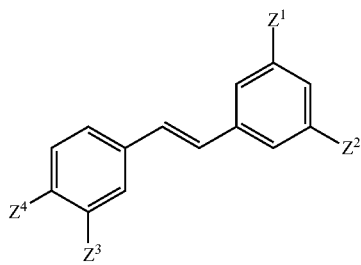

III

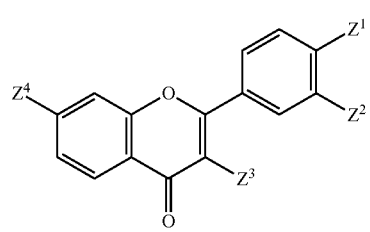

IV

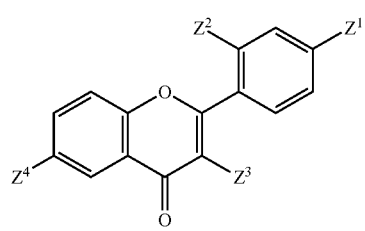

V

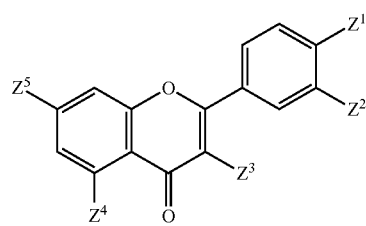

VI

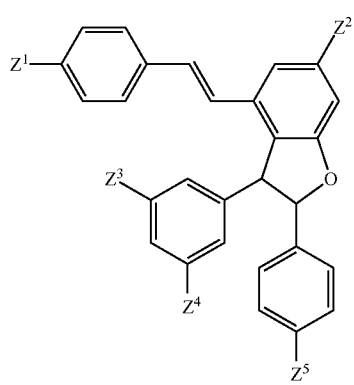

VII

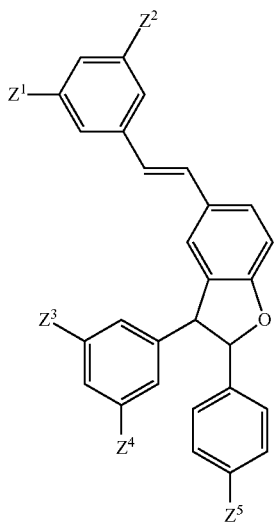

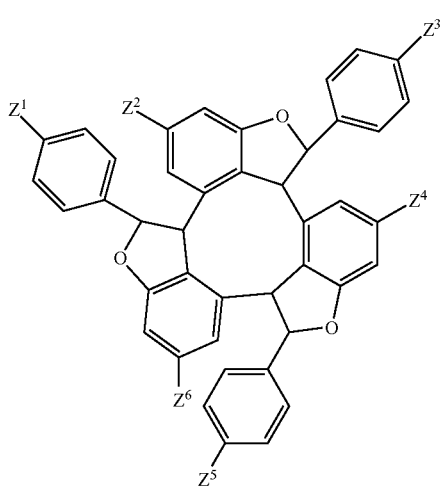

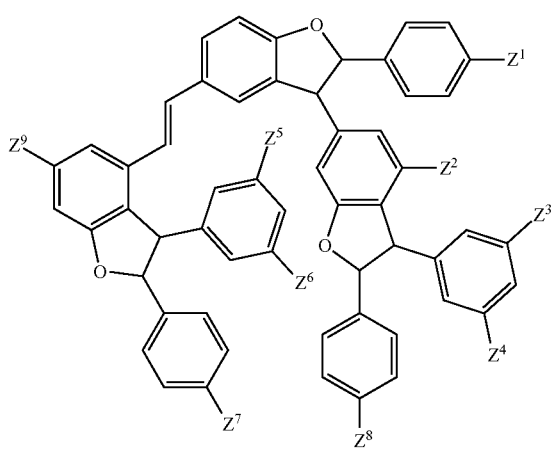

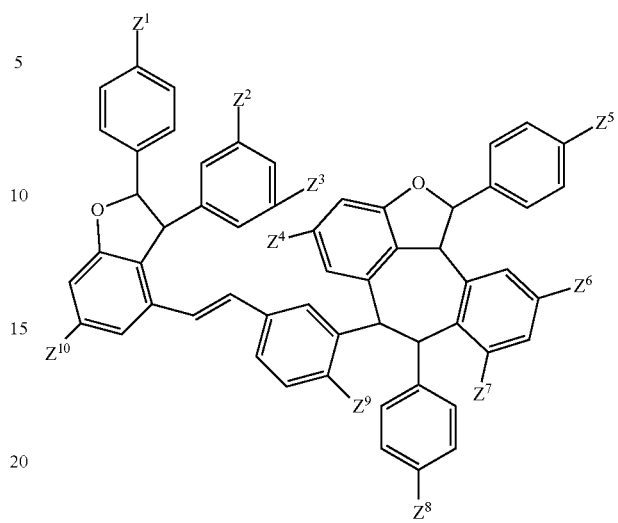

wherein $Z^1$, $Z^2$, $Z^3$, $Z^4$, $Z^5$, $Z^6$, $Z^7$, $Z^8$, $Z^9$, and $Z^{10}$ are defined herein.

In another aspect, provided herein are compounds having a structure of Formula XII or XIII or a pharmaceutically acceptable salt thereof:

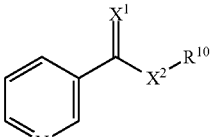

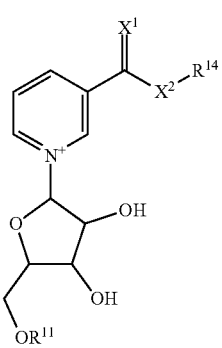

wherein $R^{10}$, $R^{11}$, $R^{14}$, $X^1$, and $X^2$ are defined herein.

In yet another aspect, the invention relates to pharmaceutical compositions comprising a compound of Formulas I-XIII and a pharmaceutically acceptable carrier.

Also, provided herein are methods and compositions for preventing or treating aging, or an aging-related disorder, a disorder associated with inflammation, or for modulating an immune response in a subject in need thereof. In some embodiments, the methods comprise administering to the subject an effective amount of a compound of Formulas I-XIII or a composition described herein.

In some embodiments, the aging-related disorder is selected from the group consisting of Alzheimer's disease, diabetes mellitus, heart disease, obesity, osteoporosis, Parkinson's disease, stroke, amniotropic lateral sclerosis, arthritis, atherosclerosis, cachexia, cancer, cardiac hypertrophy, cardiac failure, cardiac hypertrophy, cardiovascular disease, cataracts, colitis, chronic obstructive pulmonary disease, dementia, diabetes mellitus, frailty, heart disease, hepatic steatosis, high blood cholesterol, high blood pressure, Huntington's disease, hyperglycemia, hypertension, infertility, inflammatory bowel disease, insulin resistance disorder, lethargy, metabolic syndrome, muscular dystrophy, multiple sclerosis, neuropathy, nephropathy, obesity, osteoporosis, Parkinson's disease, psoriasis, retinal degeneration, sarcopenia, sleep disorders, sepsis, and stroke.

In some embodiments, the disorder associated with inflammation is selected from the group consisting of: septic shock, obesity-related inflammation, Parkinson's Disease, Crohn's Disease, Alzheimer's Disease (AD), cardiovascular disease (CVD), inflammatory bowel disease (IBD), chronic obstructive pulmonary disease, an allergic reaction, an autoimmune disease, blood inflammation, joint inflammation, arthritis, asthma, ulcerative colitis, hepatitis, psoriasis, atopic dermatitis, pemphigus, glomerulonephritis, atherosclerosis, sarcoidosis, rheumatoid arthritis, psoriatic arthritis, ankylosing spondylitis, Wegner's syndrome, Goodpasture's syndrome, giant cell arteritis, polyarteritis *nodosa*, idiopathic pulmonary fibrosis, acute lung injury, post-influenza pneumonia, SARS, tuberculosis, malaria, sepsis, cerebral malaria, Chagas disease, schistosomiasis, bacterial and viral meningitis, cystic fibrosis, multiple sclerosis, encephalomyelitis, sickle cell anemia, pancreatitis, transplantation, systemic lupus erythematosus, autoimmune diabetes, thyroiditis, and radiation pneumonitis, respiratory inflammation, and pulmonary inflammation.

In some embodiments of any of the aforementioned methods, the compound is administered in a pharmaceutically effective amount.

In some embodiments of any of the aforementioned methods, the pharmaceutically effective amount is provided as a composition (e.g., a pharmaceutical composition) in combination with a pharmaceutically-acceptable excipient, diluent, or carrier. The composition may be a cosmetic product.

The compounds and compositions disclosed herein may be administered in any formulation, including but not limited to, intravenous, oral, or topical formulations.

In some embodiments of any of the aforementioned methods, the subject is a mammal or non-mammal.

In some embodiments of any of the aforementioned methods, the subject is a human. The subject may be at least 30 years old, at least 35 years old, at least 40 years old, at least 45 years old, at least 55 years old, at least 60, or at least 65 years old.

In some embodiments, the compounds and compositions disclosed herein increase the level of NAD$^+$ and STACS for use in treating or preventing aging, or an aging-related disorder in a subject in need thereof.

In some embodiments, the compounds and compositions disclosed herein increase the level of NAD$^+$ for use in treating or preventing a disorder associated with inflammation.

In some embodiments, the compounds and compositions disclosed herein increase the level of NAD$^+$ for use in modulating an inflammatory response.

In some embodiments, the compounds and compositions disclosed herein increase the level of NAD$^+$ for use in increasing stress resistance of a cell.

In some embodiments, the compounds and compositions disclosed herein are administered conjointly with an additional sirtuin-activating compound.

DETAILED DESCRIPTION

Disclosed herein are hybrid compounds of STACS and NPs, and pharmaceutical compositions thereof. In some embodiments, hybrid compounds have enhanced stability and improved pharmacokinetics. Also, provided herein are methods for preventing or treating aging, or an aging-related disorder by administering to the subject an effective amount of a compound of Formulas I-XIII or a composition described herein. Also provided herein are methods for treating or preventing a disorder associated with inflammation in a subject in need thereof comprising administering to the subject an effective amount a compound of Formulas I-XIII or a composition described herein. In some aspects, disclosed herein are methods of modulating an inflammatory response in a subject in need thereof by administering to the subject an effective amount of a compound of Formulas I-XIII or a composition described herein. In some aspects, provided herein are compounds and compositions that improve the bioefficacy and bioavailability of resveratrol. Compounds and compositions provided herein may result in slow phase II metabolism and excretion of resveratrol, enhanced ability to penetrate the biomembranes, and increased shelf life. In some embodiments, the compounds and compositions disclosed herein may act to increase the level or activity of nicotinamide dinucleotides (e.g., NAD$^+$, NMN; NAD$^+$ precursor pathways, such as a protein selected from the group consisting of NPT1, PNC1, NMA1 and NMA2; or NAD$^+$ biosynthesis, such as enzymes selected from NMNAT-1, -2, and/or -3 or NAMPT). In some embodiments, the compounds and compositions disclosed herein may increase the activation of SIRT1.

I. COMPOUNDS

In certain embodiments, the invention relates to compounds having a structure of Formula I or a pharmaceutically acceptable salt thereof:

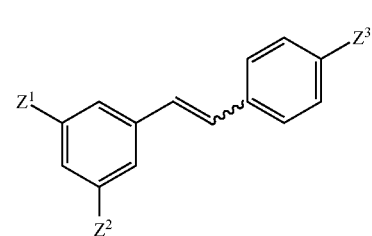

I wherein $Z^1$, $Z^2$, and $Z^3$ are each independently selected from hydroxyl, —OR$^5$, —OC(O)-L$^1$-R$^1$, —OC(NR$^6$)-L$^1$-R$^1$, and

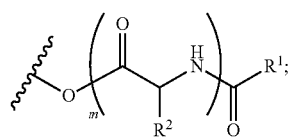

L¹ is absent or a linker group selected from

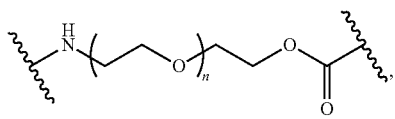

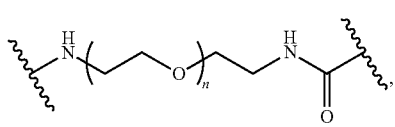

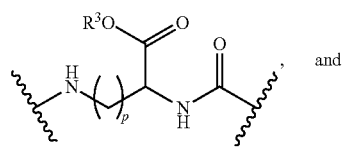
and

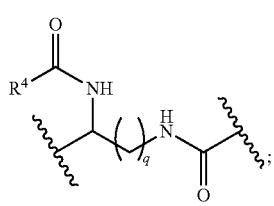

R¹ is optionally substituted alkyl, heteroalkyl, alkenyl, aryl or heteroaryl;

R² is independently selected from H, optionally substituted alkyl, heteroalkyl, aralkyl, and heteroaralkyl;

R³ is selected from H, optionally substituted alkyl, heteroalkyl, aryl, and heteroaryl;

R⁴ is selected from H, optionally substituted alkyl, heteroalkyl, alkenyl, aryl, and heteroaryl;

R⁵ is selected from H, optionally substituted alkyl, cycloalkyl, heteroalkyl and heterocyclyl;

R⁶ is selected from H and alkyl; and m, n, p, q are each independently an integer selected from 1 to 10;

provided that $Z^1$, $Z^2$, and $Z^3$ are not all hydroxyl.

In some embodiments, the compound has the structure of Formula Ia or a pharmaceutically acceptable salt thereof:

Ia

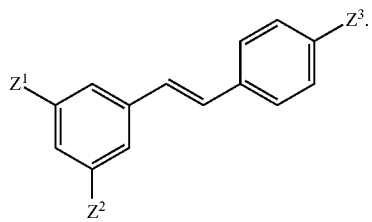

In some embodiments, the compound has the structure of Formula Ib or a pharmaceutically acceptable salt thereof:

Ib

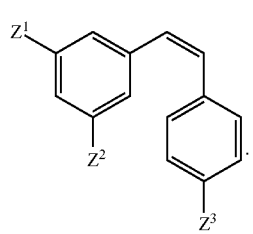

In certain other embodiments, the invention relates to compounds having a structure of Formula II, III, IV, or V or a pharmaceutically acceptable salt thereof:

II

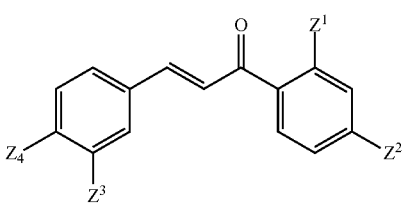

III

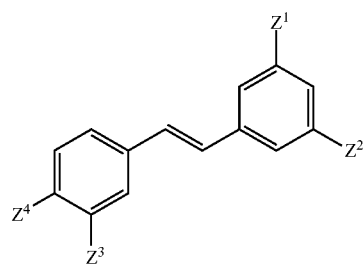

IV

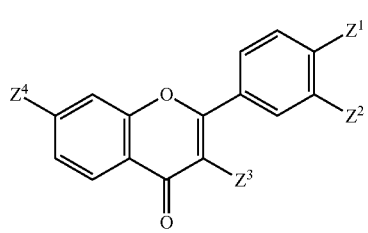

V

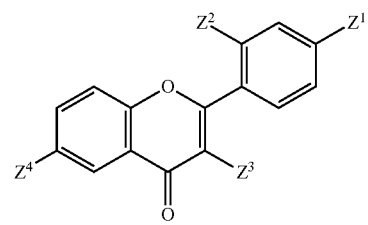

wherein $Z^1$, $Z^2$, $Z^3$ and $Z^4$ are each independently selected from hydroxyl, —OR⁵, —OC(O)-L¹-R¹, —OC(NR⁶)-L¹-R¹, and

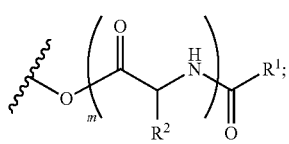

L¹ is absent or a linker group selected from

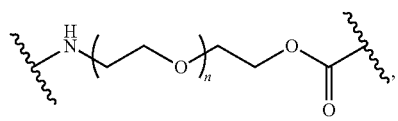

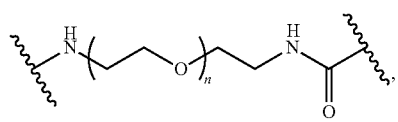

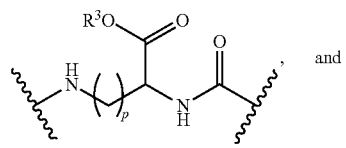 and

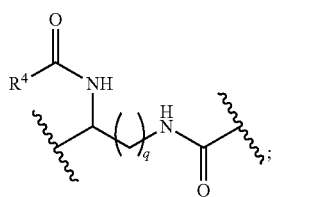

R¹ is optionally substituted alkyl, heteroalkyl, alkenyl, aryl or heteroaryl;

R² is independently selected from H, optionally substituted alkyl, heteroalkyl, aralkyl, and heteroaralkyl;

R³ is selected from H, optionally substituted alkyl, heteroalkyl, aryl, and heteroaryl;

R⁴ is selected from H, optionally substituted alkyl, heteroalkyl, alkenyl, aryl, and heteroaryl;

R⁵ is selected from H, optionally substituted alkyl, cycloalkyl, heteroalkyl and heterocyclyl;

R⁶ is selected from H and alkyl; and m, n, p, q are each independently an integer from 1 to 10;

provided that $Z^1$, $Z^2$, $Z^3$ and $Z^4$ are not all hydroxyl.

In certain other embodiments, the invention relates to compounds having a structure of Formula VI, VII, or VIII or a pharmaceutically acceptable salt thereof:

VI

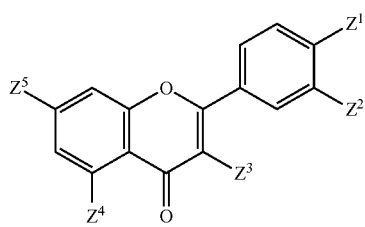

VII

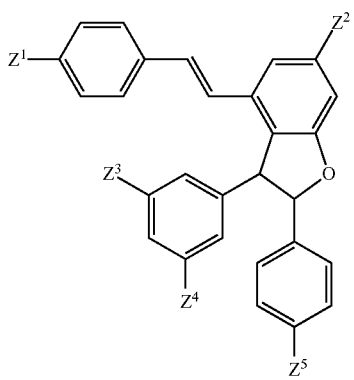

VIII

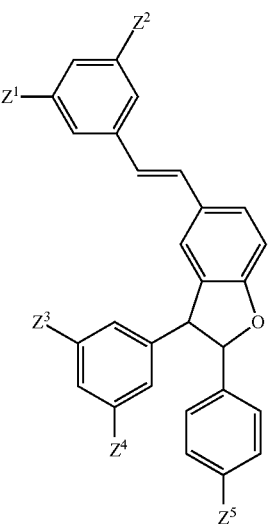

wherein $Z^1$, $Z^2$, $Z^3$, $Z^4$ and $Z^5$ are each independently selected from hydroxyl, —OR⁵, —OC(O)-L¹-R¹, —OC(NR⁶)-L¹R¹, and

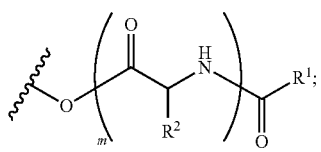

L¹ is absent or a linker group selected from

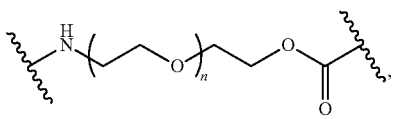

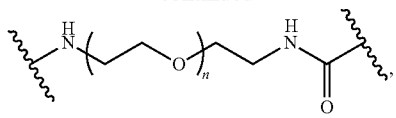

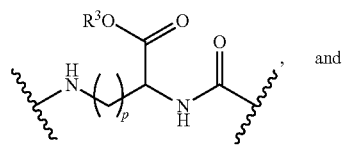

and

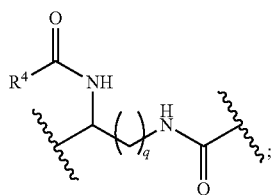

$R^1$ is optionally substituted alkyl, heteroalkyl, alkenyl, aryl or heteroaryl;

$R^2$ is independently selected from H, optionally substituted alkyl, heteroalkyl, aralkyl, and heteroaralkyl;

$R^3$ is selected from H, optionally substituted alkyl, heteroalkyl, aryl, and heteroaryl;

$R^4$ is selected from H, optionally substituted alkyl, heteroalkyl, alkenyl, aryl, and heteroaryl;

$R^5$ is selected from H, optionally substituted alkyl, cycloalkyl, heteroalkyl and heterocyclyl;

$R^6$ is selected from H and alkyl; and m, n, p, q are each independently an integer selected from 1 to 10;

provided that $Z^1$, $Z^2$, $Z^3$, $Z^4$ and $Z^5$ are not all hydroxyl.

In certain other embodiments, the invention relates to compounds having a structure of Formula IX, X or XI or a pharmaceutically acceptable salt thereof:

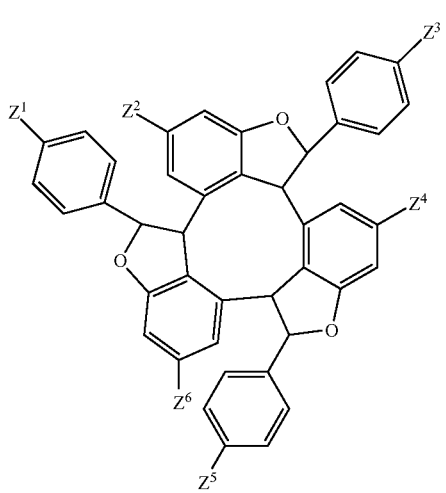

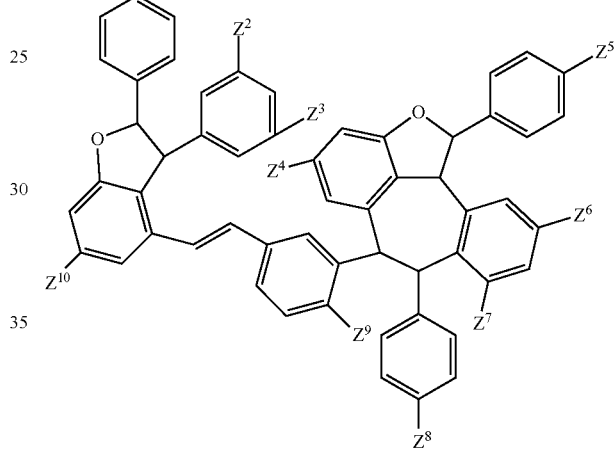

wherein $Z^1$, $Z^2$, $Z^3$, $Z^4$, $Z^5$, $Z^6$, $Z^7$, $Z^8$, $Z^9$, and $Z^{10}$ are each independently selected from hydroxyl, —$OR^5$, —OC(O)-$L^1R^1$, —OC($NR^6$)-$L^1$-$R^1$, and

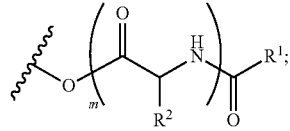

$L^1$ is absent or a linker group selected from

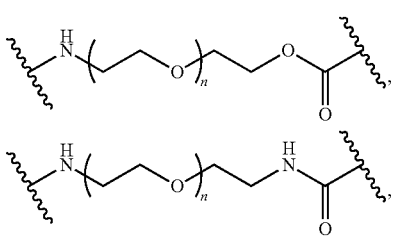

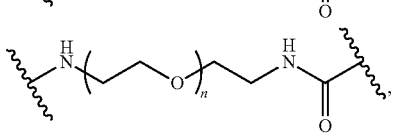

-continued

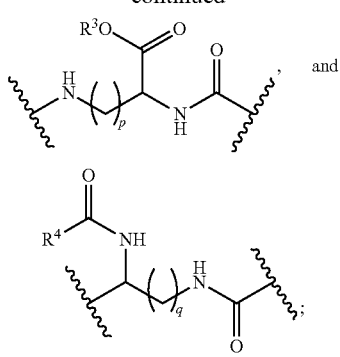
and $R^1$ is optionally substituted alkyl, heteroalkyl, alkenyl, aryl or heteroaryl;

$R^2$ is independently selected from H, optionally substituted alkyl, heteroalkyl, aralkyl, and heteroaralkyl;

$R^3$ is selected from H, optionally substituted alkyl, heteroalkyl, aryl, and heteroaryl;

$R^4$ is selected from H, optionally substituted alkyl, heteroalkyl, alkenyl, aryl, and heteroaryl;

$R^5$ is selected from H, optionally substituted alkyl, cycloalkyl, heteroalkyl and heterocyclyl;

$R^6$ is selected from H and alkyl; and m, n, p, q are each independently an integer selected from 1 to 10;

provided that $Z^1$, $Z^2$, $Z^3$, $Z^4$, $Z^5$, $Z^6$, $Z^7$, $Z^8$, $Z^9$, and $Z^{10}$ are not all hydroxyl.

In some embodiments, $Z^1$ is hydroxyl. In some embodiments, $Z^1$ and $Z^2$ are hydroxyl. In some embodiments, $Z^1$, $Z^2$, $Z^3$, $Z^4$ and $Z^5$ are the same (e.g., $Z^1=Z^2=Z^3$, $Z^1=Z^2=Z^3=Z^4$, $Z^1=Z^2=Z^3=Z^4=Z^5$, $Z^1=Z^2=Z^3=Z^4=Z^5=Z^6$, $Z^1=Z^2=Z^3=Z^4=Z^5=Z^6=Z^7=Z^8$, $Z^1=Z^2=Z^3=Z^4=Z^5=Z^6=Z^7=Z^8=Z^9=Z^{10}$).

In some embodiments, $R^1$ is optionally substituted heteroaryl. In some embodiments, $R^1$ comprises a nitrogen heteroatom. In some embodiments, $R^1$ is optionally substituted pyridyl. In some embodiments, $R^1$ is substituted with a ribosyl group or a ribosyl monophosphate group. In some embodiments, $R^1$ is

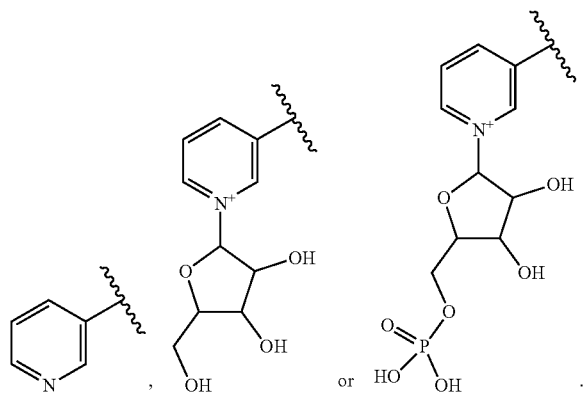 [SMILES: *c1cccnc1 ; *c1ccc[n+](C2OC(CO)C(O)C2O)c1 ; *c1ccc[n+](C2OC(COP(=O)(O)O)C(O)C2O)c1]

In some embodiments, $R^1$ is

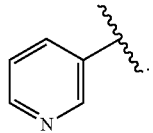

In some embodiments, $R^1$ is

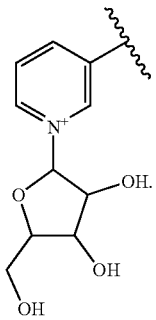 [SMILES: *c1ccc[n+](C2OC(CO)C(O)C2O)c1]

In some embodiments, $R^1$ is

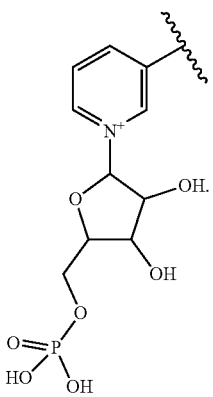 [SMILES: *c1ccc[n+](C2OC(COP(=O)(O)O)C(O)C2O)c1]

In some embodiments, $R^1$ is optionally substituted alkyl, heteroalkyl, or alkenyl. In some embodiments, $R^1$ is optionally substituted alkyl. In some embodiments, $R^1$ is straight chained alkyl group having 10 to 20 carbon atoms. In some embodiments, $R^1$ has 15 carbon atoms. In some embodiments, $R^1$ is

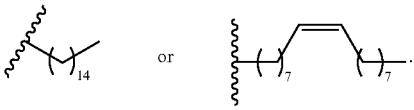

In some embodiments, n is selected from 3, 4, 5, and 6. In some embodiments, q is 3, 4, or 5. In some embodiments, q is 4. In some embodiments, p is 3, 4, or 5. In some embodiments, p is 4.

In some embodiments, $R^4$ is straight chained alkyl group having 10 to 20 carbon atoms. In some embodiments, $R^4$ has 15 carbon atoms. In some embodiments, $R^4$ is

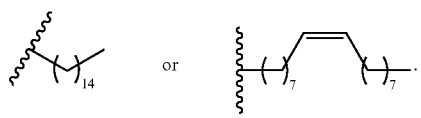

In some embodiments, $R^3$ is —$CH_3$. In some embodiments, $R^3$ is an alkyl group having 2 to 20 carbon atoms. In some embodiments, $R^3$ is an alkyl group having 2 to 16 carbon atoms.

In some embodiments, each $R^2$ is independently selected from H,

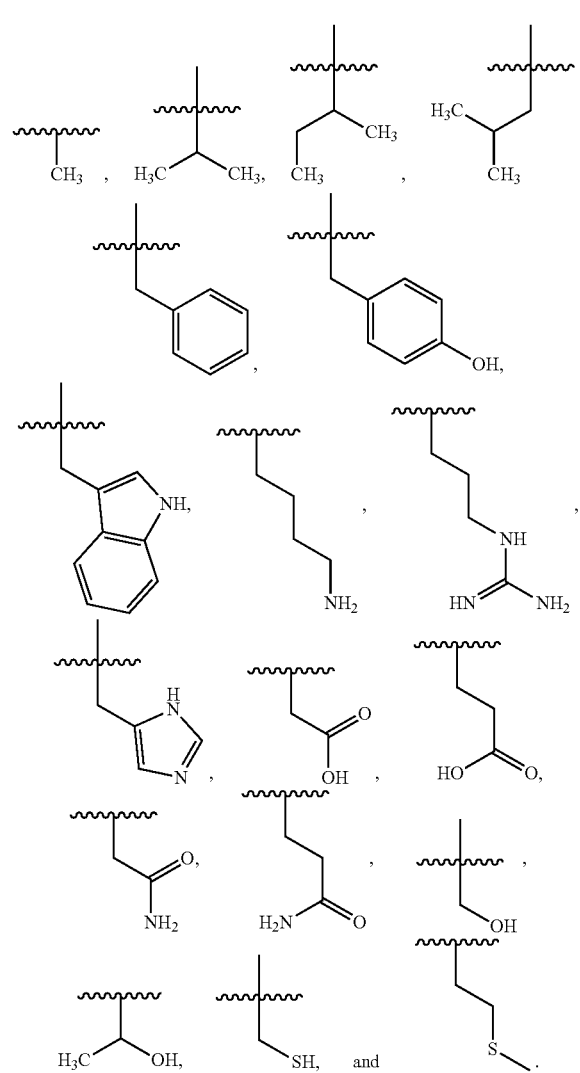

some embodiments, $R^2$ is selected from H,

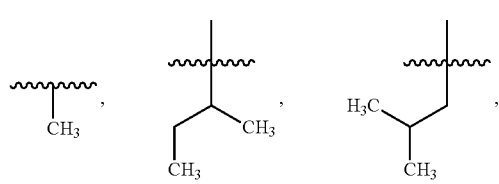

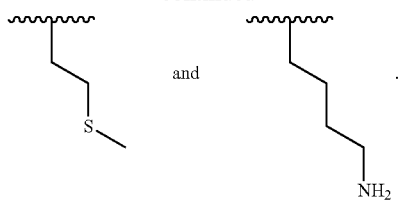

In some embodiments, $R^2$ is selected from H,

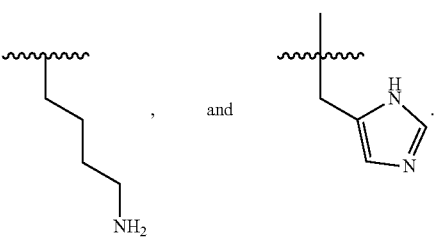 [SMILES: *CCCCN ; *Cc1cnc[nH]1]

In some embodiments, m is selected from 2, 3, 4, 5, 6, 7, and 8. In some embodiments, m is selected from 3, 4, 5, 6, and 7. In some embodiments, m is 3.

In some embodiments, $Z^1$, $Z^2$, and $Z^3$ is

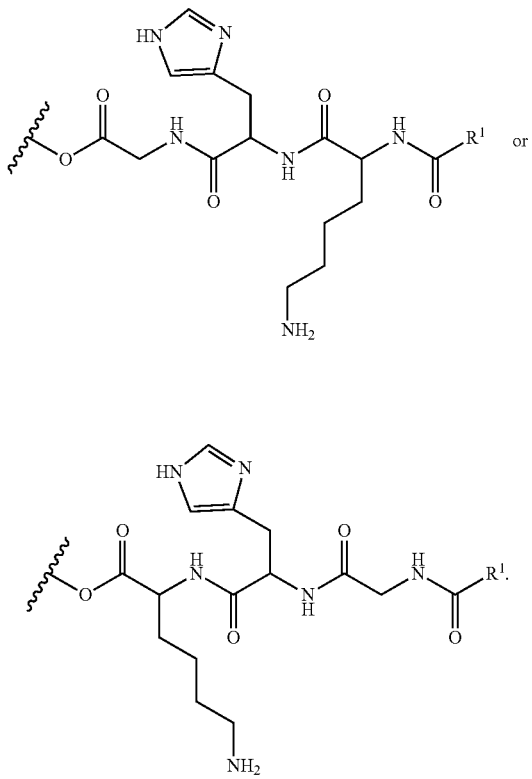

In some embodiments, $R^5$ is optionally substituted heterocyclyl. For example, in some embodiments, $R^5$ is heterocyclyl substituted with hydroxyl In some embodiments, $Z^1$, $Z^2$, $Z^3$, $Z^4$, $Z^5$, $Z^6$, $Z^7$, $Z^8$, $Z^9$, and $Z^{10}$ are each independently selected from

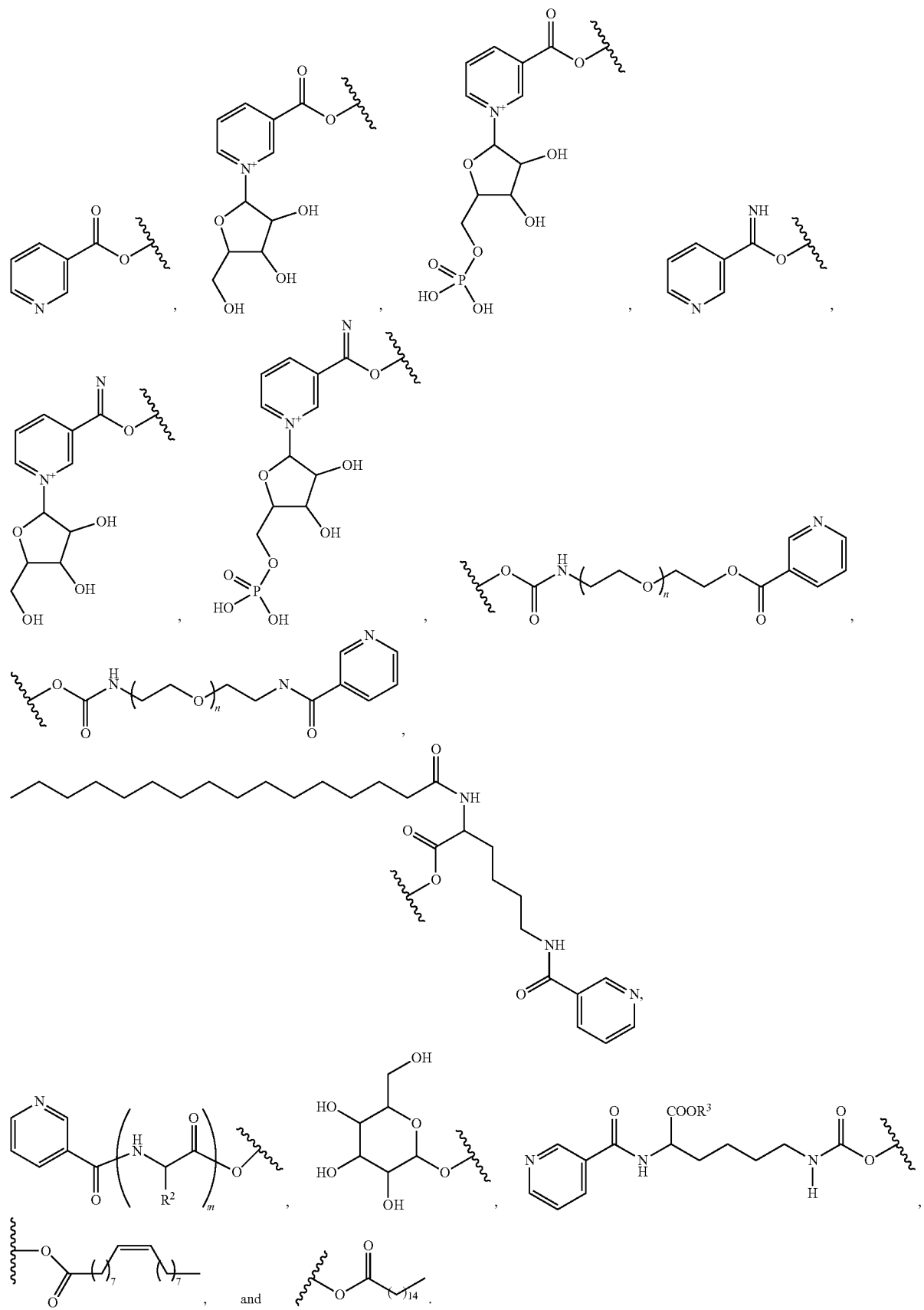

Also provided herein are compounds having a structure of Formula XII or XIII or a pharmaceutically acceptable salt thereof:

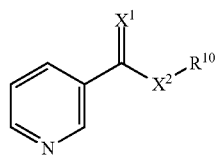

XII

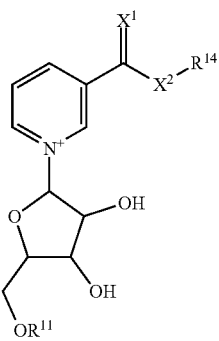

XIII wherein
$X^1$ is selected from O and S;
$X^2$ is selected from O and NH;
$X^3$ is selected from O and S;
$X^4$ is selected from O and NH;
$R^{10}$ is selected from H, optionally substituted alkyl, heteroalkyl, alkenyl, heteroalkenyl, acyl, aryl

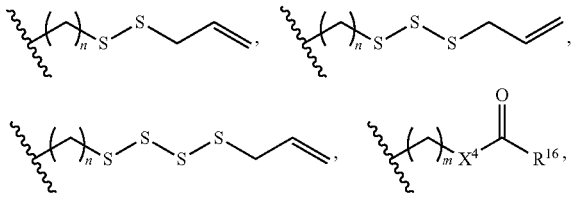

and heteroaryl;
$R^{11}$ is selected from H and

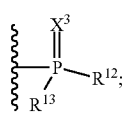

and
$R^{12}$ and $R^{13}$ are each independently selected form —SH, —OH, and alkoxy;
$R^{14}$ is selected from H, optionally substituted alkyl, heteroalkyl, alkenyl, heteroalkenyl, acyl, aryl,

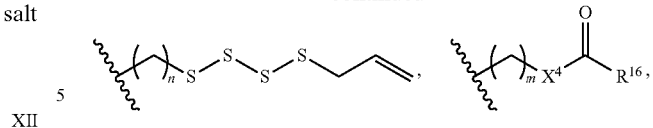

and heteroaryl;
$R^{16}$ is selected from optionally substituted alkyl, heteroalkyl, alkenyl, and heteroalkenyl; and
m and n are each independently an integer selected from 1 to 10,
  provided that when
    i) $R^{14}$ is H, at least one of when $X^1$, $X^2$ and $X^3$ is S
    ii) $X^2$ is O and $X^4$ is NH, $R^{16}$ is not

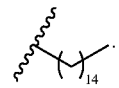

In some embodiments, $X^1$ is O. In some embodiments, $X^1$ is S. In some embodiments, $X^2$ is O. In some embodiments, $X^3$ is O.

In some embodiments, $R^{10}$ is optionally substituted aryl. In some embodiments, $R^{10}$ is optionally substituted phenyl. In some embodiments, $R^{10}$ is

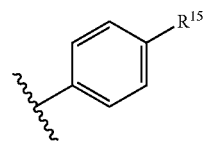

and $R^{15}$ is selected from cycloalkyl and heterocyclyl.
In some embodiments, $R^{15}$ is a heterocyclyl comprising at least one S. In some embodiments, $R^{15}$ is a heterocyclyl comprising at least two S. In some embodiments, $R^{10}$ is optionally substituted heteroalkenyl. In some embodiments, $R^{15}$ is a heteroalkenyl comprising at least one S. In some embodiments, $R^{15}$ is a heteroalkenyl comprising at least two S.

In some embodiments, $R^{10}$ is selected from

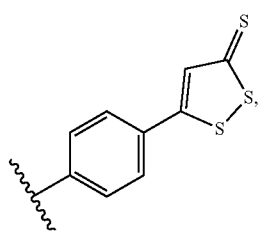

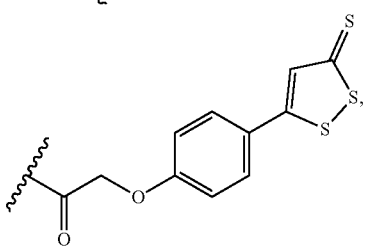

21

-continued

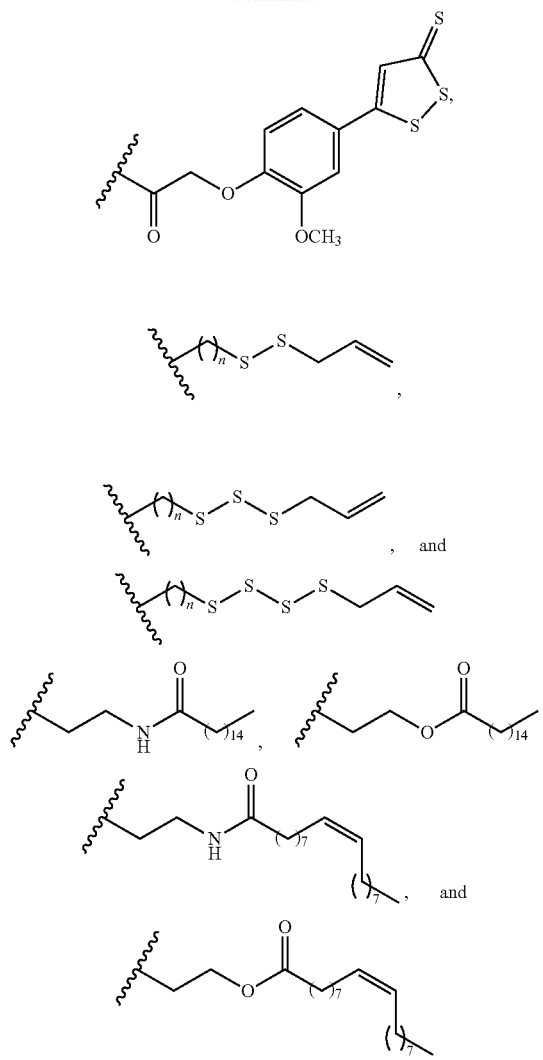

, and and m and n are each independently an integer from 1 to 5. In some embodiments, n is 1 or 3. In Some Embodiments, m is 2.

In some embodiments, $R^{14}$ is optionally substituted aryl. In some embodiments, $R^{14}$ is optionally substituted phenyl. In some embodiments, $R^{14}$ is

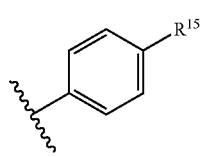

and $R^{15}$ is selected from cycloalkyl and heterocyclyl.

In some embodiments, $R^{15}$ is a heterocyclyl comprising at least one S. In some embodiments, $R^{15}$ is a heterocyclyl comprising at least two S. In some embodiments, $R^{10}$ is optionally substituted heteroalkenyl. In some embodiments, $R^{15}$ is a heteroalkenyl comprising at least one S. In some embodiments, $R^{15}$ is a heteroalkenyl comprising at least two S.

22

In some embodiments, $R^{14}$ is selected from

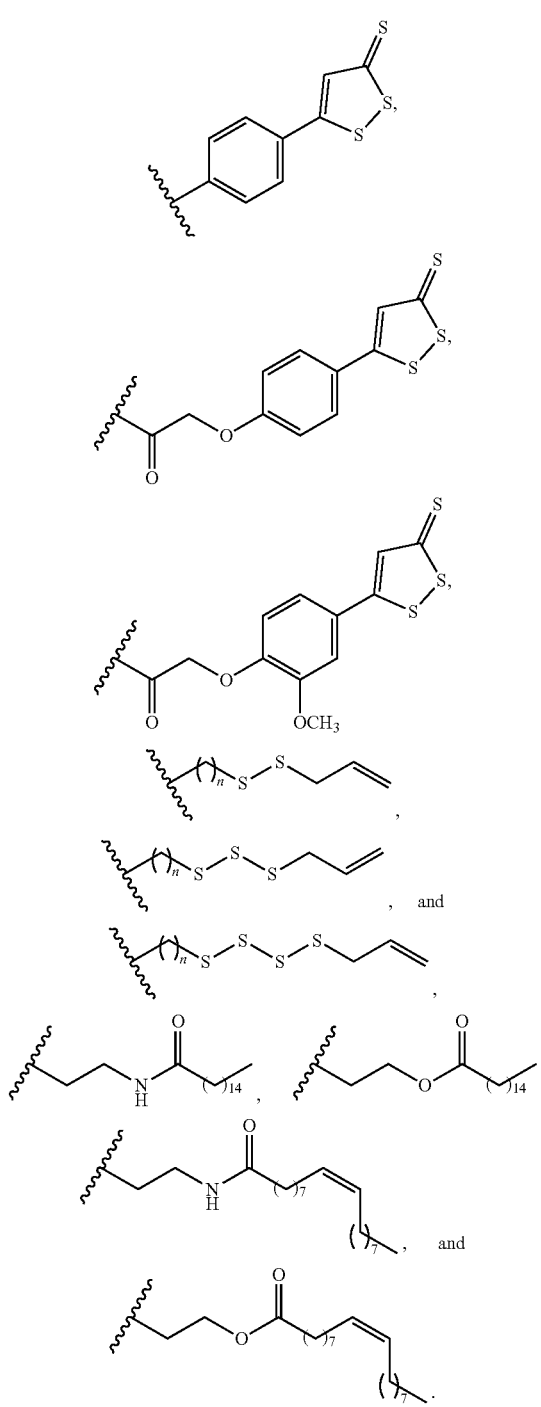

and n is an integer from 1 to 5. In some embodiments, n is 1 or 3.

In some embodiments, $R^{16}$ is alkyl or alkenyl. In some embodiments, $R^{16}$ is optionally substituted alkyl, heteroalkyl, or alkenyl. In some embodiments, $R^{16}$ is optionally substituted alkyl. In some embodiments, $R^{16}$ is straight chained alkyl group having 10 to 20 carbon atoms. In some embodiments, $R^{16}$ has 15 carbon atoms. In some embodiments, $R^{16}$ is or

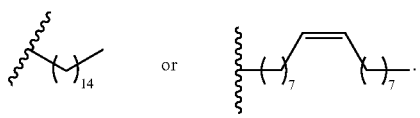

In certain embodiments, compounds of the invention may be racemic. In certain embodiments, compounds of the invention may be enriched in one enantiomer. For example, a compound of the invention may have greater than 30% ee, 40% ee, 50% ee, 60% ee, 70% ee, 80% ee, 90% ee, or even 95% or greater ee. The compounds of the invention have more than one stereocenter. Consequently, compounds of the invention may be enriched in one or more diastereomer. For example, a compound of the invention may have greater than 30% de, 40% de, 50% de, 60% de, 70% de, 80% de, 90% de, or even 95% or greater de.

In certain embodiments, as will be described in detail below, the present invention relates to methods of treating or preventing a disease or condition with a compound of Formula I-XIII, or a pharmaceutically acceptable salt thereof. In certain embodiments, the therapeutic preparation may be enriched to provide predominantly one enantiomer of a compound of Formula I-XIII. An enantiomerically enriched mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, the therapeutic preparation may be enriched to provide predominantly one diastereomer of a compound of Formulas I-XIII. A diastereomerically enriched mixture may comprise, for example, at least 60 mol percent of one diastereomer, or more preferably at least 75, 90, 95, or even 99 mol percent.

In certain embodiments, the present invention provides a pharmaceutical preparation suitable for use in a human patient in the treatment of a disease or condition, comprising an effective amount of any compound of Formulas I-XIII, and one or more pharmaceutically acceptable excipients. In certain embodiments, the pharmaceutical preparations may be for use in treating or preventing a condition or disease as described herein. In certain embodiments, the pharmaceutical preparations have a low enough pyrogen activity to be suitable for use in a human patient.

Compounds of any of the above structures may be used in the manufacture of medicaments for the treatment of any diseases or conditions disclosed herein.

Exemplary compounds disclosed herein (e.g., compounds of Formula I-XIII) are depicted in Tables 1 and 2. The compounds of Tables 1 and 2 are understood to encompass both the free base and the conjugate acid. For example, the compounds in Table 1 or 2 may be depicted as complexes or salts with trifluoroacetic acid or hydrochloric acid, but the compounds in their corresponding free base forms or as salts with other acids are equally within the scope of the invention. Compounds may be isolated in either the free base form, as a salt (e.g., a hydrochloride salt) or in both forms. In the chemical structures shown below, standard chemical abbreviations are sometimes used.

TABLE 1

Exemplary Compounds of Formula I-XI

| Compound | Compound Number |
|---|---|
| 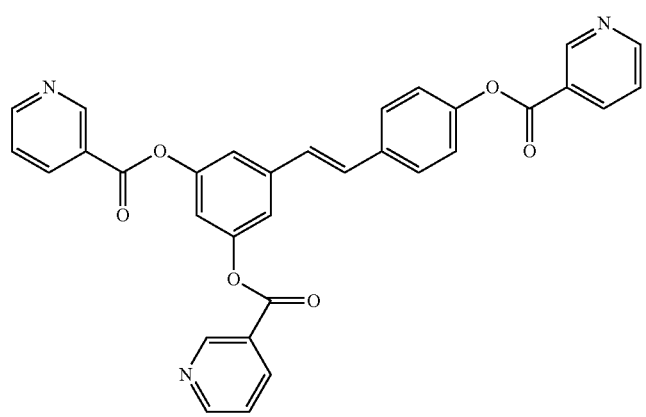 [SMILES: O=C(Oc1ccc(/C=C/c2cc(OC(=O)c3cccnc3)cc(OC(=O)c3cccnc3)c2)cc1)c1cccnc1] | 1 |

TABLE 1-continued

Exemplary Compounds of Formula I-XI

| Compound | Compound Number |
|---|---|
| | 2 |
| | 3 |

TABLE 1-continued

Exemplary Compounds of Formula I-XI

| Compound | Compound Number |
|---|---|
| (structure) | 4 |
| (structure) | 5 |
| (structure) | 6 |

TABLE 1-continued

Exemplary Compounds of Formula I-XI

| Compound | Compound Number |
|---|---|
| (structure) | 7 |
| (structure) | 8 |
| (structure) | 9 |

TABLE 1-continued

Exemplary Compounds of Formula I-XI

| Compound | Compound Number |
|---|---|
| | 10 |
| | 11 |
| | 12 |

TABLE 1-continued
Exemplary Compounds of Formula I-XI
| Compound | Compound Number |
|---|---|
| 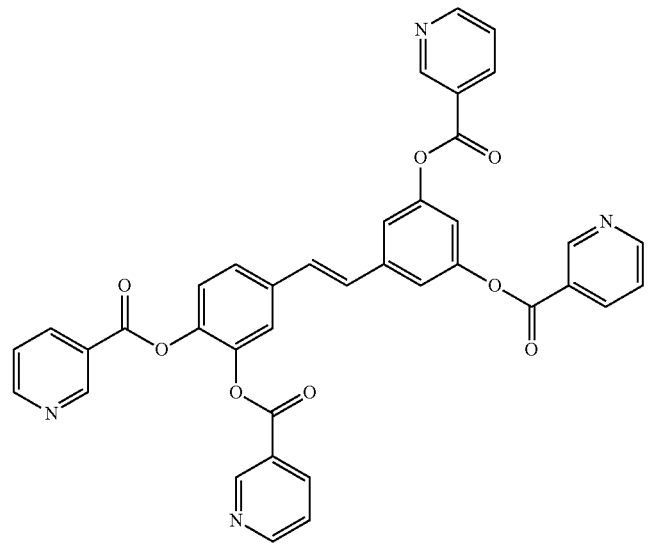 [SMILES: O=C(Oc1cc(/C=C/c2ccc(OC(=O)c3cccnc3)c(OC(=O)c3cccnc3)c2)cc(OC(=O)c2cccnc2)c1)c1cccnc1] | 13 |
| 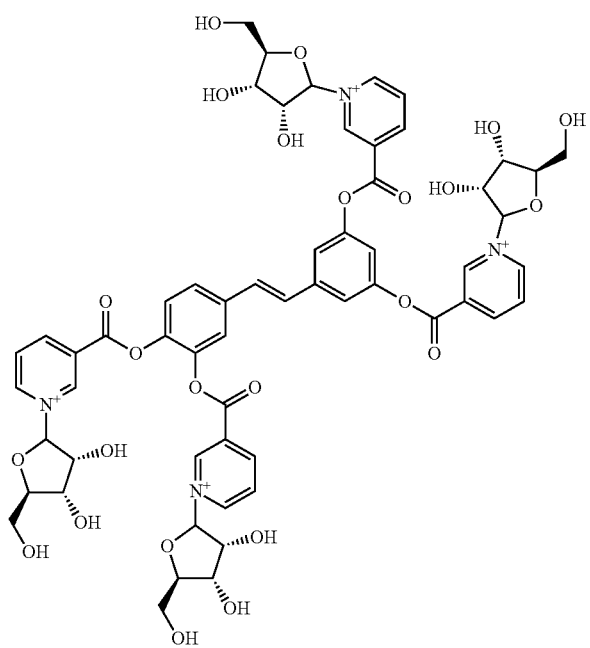 [SMILES: O=C(Oc1cc(/C=C/c2ccc(OC(=O)c3ccc[n+](C4O[C@H](CO)[C@@H](O)[C@H]4O)c3)c(OC(=O)c3ccc[n+](C4O[C@H](CO)[C@@H](O)[C@H]4O)c3)c2)cc(OC(=O)c2ccc[n+](C3O[C@H](CO)[C@@H](O)[C@H]3O)c2)c1)c1ccc[n+](C2O[C@H](CO)[C@@H](O)[C@H]2O)c1] | 14 |

TABLE 1-continued

Exemplary Compounds of Formula I-XI

| Compound | Compound Number |
|---|---|
| | 15 |
| | 16 |
| | 17 |

TABLE 1-continued

Exemplary Compounds of Formula I-XI

| Compound | Compound Number |
|---|---|
| | 18 |
| | 19 |

TABLE 1-continued
Exemplary Compounds of Formula I-XI
| Compound | Compound Number |
|---|---|
| | 20 |
| | 21 |
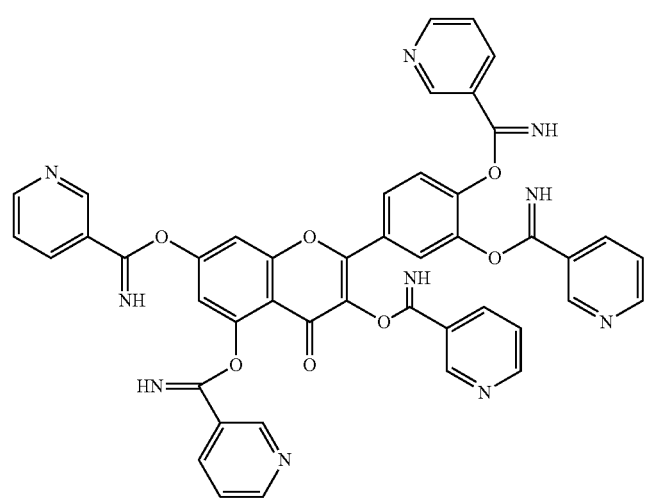 [SMILES: N=C(Oc1cc(OC(=N)c2cccnc2)c2c(=O)c(OC(=N)c3cccnc3)c(-c3ccc(OC(=N)c4cccnc4)c(OC(=N)c4cccnc4)c3)oc2c1)c1cccnc1]

TABLE 1-continued
Exemplary Compounds of Formula I-XI
| Compound | Compound Number |
|---|---|
| 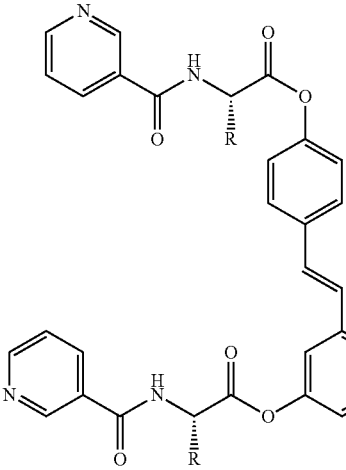 | |
| 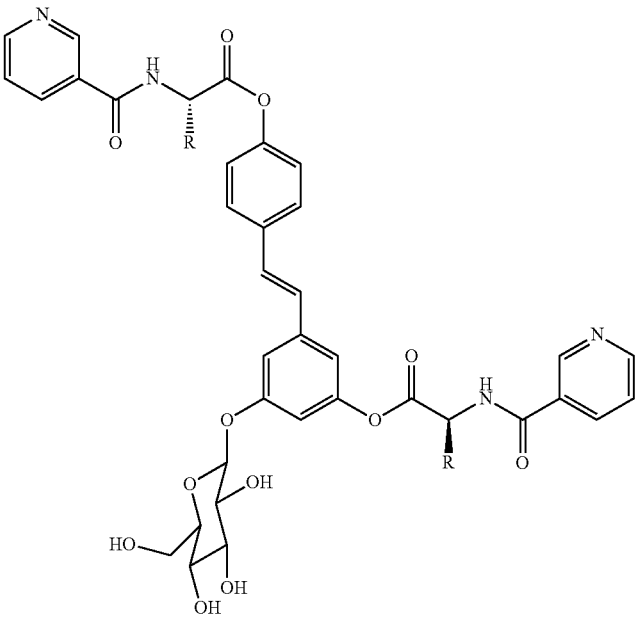 | |

TABLE 1-continued

Exemplary Compounds of Formula I-XI

| Compound | Compound Number |
|---|---|
| | 52 |
| | 53 |

TABLE 1-continued
Exemplary Compounds of Formula I-XI
| Compound | Compound Number |
|---|---|
| 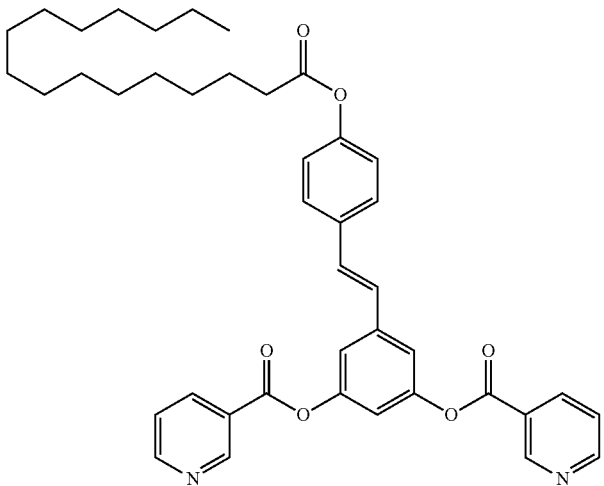 [SMILES: CCCCCCCCCCCCCCCC(=O)Oc1ccc(/C=C/c2cc(OC(=O)c3cccnc3)cc(OC(=O)c3cccnc3)c2)cc1] | 54 |
| 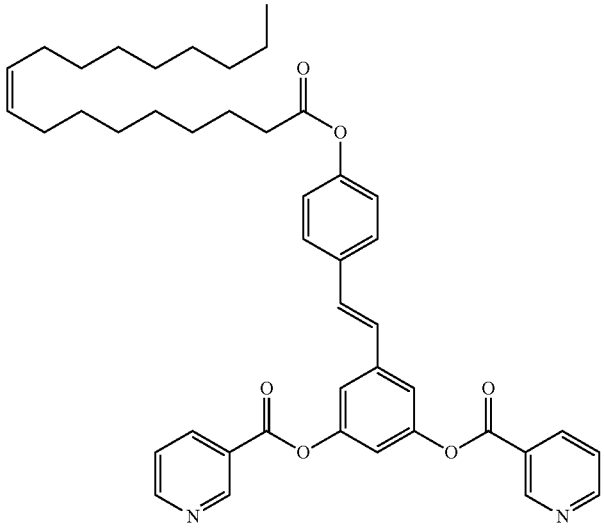 [SMILES: CCCCCCCC/C=C\CCCCCCCC(=O)Oc1ccc(/C=C/c2cc(OC(=O)c3cccnc3)cc(OC(=O)c3cccnc3)c2)cc1] | 55 |
R = H, —CH₃, 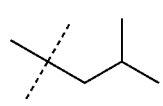 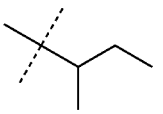 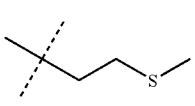
Gly    Ala    Leu    Ile    Met TABLE 2
Exemplary Compounds of Formulas XII and XIII
| Compound | Compound Number |
|---|---|
| 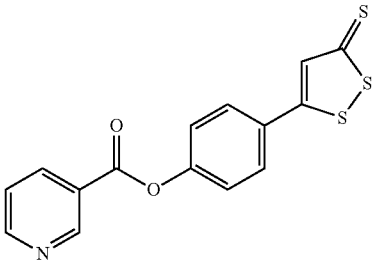 [SMILES: O=C(Oc1ccc(-c2cc(=S)ss2)cc1)c1cccnc1] | 22 |
| 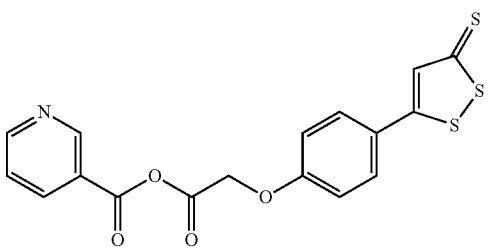 [SMILES: O=C(COc1ccc(-c2cc(=S)ss2)cc1)OC(=O)c1cccnc1] | 23 |
| 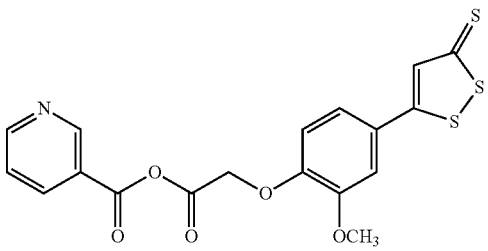 [SMILES: COc1cc(-c2cc(=S)ss2)ccc1OCC(=O)OC(=O)c1cccnc1] | 24 |
| 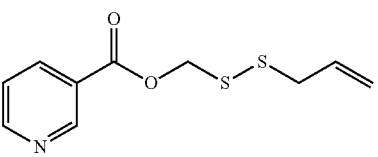 | 25 |
| 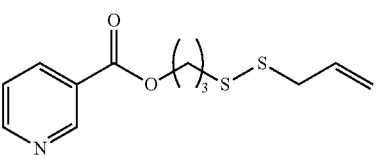 | 26 |
| 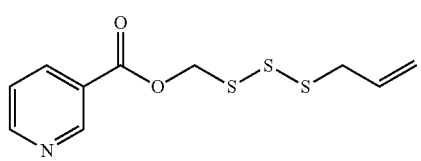 [SMILES: C=CCSSSCOC(=O)c1cccnc1] | 27 |
| 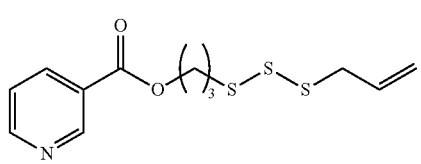 | 28 |

TABLE 2-continued

Exemplary Compounds of Formulas XII and XIII

| Compound | Compound Number |
|---|---|
| | 29 |
| | 30 |
| | 32 |
| | 33 |
| | 34 |

TABLE 2-continued

Exemplary Compounds of Formulas XII and XIII

| Compound | Compound Number |
|---|---|
| (structure: nicotinamide riboside 5′-O-thiophosphate with OH, OH on phosphorus) | 35 |
| (structure: nicotinic acid riboside 5′-O-(O-methyl thiophosphate) with SH) | 36 |
| (structure: nicotinamide riboside 5′-O-(O-methyl thiophosphate) with SH) | 37 |
| (structure: nicotinamide riboside with 3-carboxylate ester linked to 4-(3-thioxo-3H-1,2-dithiol-5-yl)phenyl group) | 38 |

TABLE 2-continued

Exemplary Compounds of Formulas XII and XIII

| Compound | Compound Number |
|---|---|
| (structure) | 39 |
| (structure) | 40 |
| (structure) | 41 |
| (structure) | 42 |
| (structure) | 43 |

TABLE 2-continued

Exemplary Compounds of Formulas XII and XIII

| Compound | Compound Number |
|---|---|
| (nicotinate-O-CH₂CH₂-O-C(O)-(CH₂)₁₄-CH₃ structure) | 44 |
| (nicotinate-O-CH₂CH₂-O-C(O)-(CH₂)₇-CH=CH-(CH₂)₇-CH₃ structure) | 45 |
| (nicotinate-O-CH₂CH₂-NH-C(O)-(CH₂)₇-CH=CH-(CH₂)₇-CH₃ structure) | 46 |
| (nicotinamide-NH-CH₂CH₂-O-C(O)-(CH₂)₁₄-CH₃ structure) | 47 |
| (nicotinamide-NH-CH₂CH₂-NH-C(O)-(CH₂)₁₄-CH₃ structure) | 48 |
| (nicotinamide-NH-CH₂CH₂-O-C(O)-(CH₂)₇-CH=CH-(CH₂)₇-CH₃ structure) | 49 |
| (nicotinamide-NH-CH₂CH₂-NH-C(O)-(CH₂)₇-CH=CH-(CH₂)₇-CH₃ structure) | 50 |

TABLE 3

Other Compounds

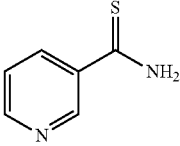

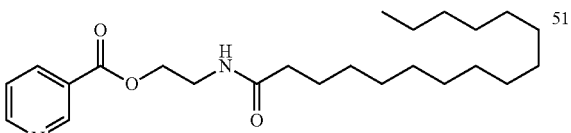

As discussed herein, in some embodiments, the compounds disclosed herein are hybrid compounds of STACS and NPs. Exemplary STACS suitable to modification as disclosed herein include, but are not limited to, resveratrol, viniferin, (e.g., alpha-viniferin, beta-viniferin, delta-viniferin, epsilon-viniferin, gamma-viniferin, R-viniferin (stilbenoid vitisin B), R2-viniferin (stilbenoid vitisin A), quercetin, fisetin, piceatannol, butein, 3,6,2'4'-tertrahydroxyflavoine, trans-piced, and cis-piceid

II—PHARMACEUTICAL COMPOSITIONS

In certain other aspects, provided herein are pharmaceutical compositions comprising a compound disclosed herein and a pharmaceutically acceptable carrier As described in detail below, the pharmaceutical compositions and/or compounds disclosed herein may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; or (2) parenteral administration, for example, by subcutaneous, intramuscular, intravenous, intrathecal, intracerebral or epidural injection as, for example, a sterile solution or suspension, or sustained-release formulation. Methods of preparing pharmaceutical formulations or compositions include the step of bringing into association a compound described herein (e.g., a compound of Formula I) with the carrier and, optionally, one or more accessory ingredients. In general, the formulations are prepared by uniformly and intimately bringing into association an agent described herein with liquid carriers, or finely divided solid carriers, or both, and then, if necessary, shaping the product.

Pharmaceutical compositions for use in accordance with the present methods may be formulated in conventional manner using one or more physiologically acceptable carriers or excipients. Thus, compounds and compositions described herein and their physiologically acceptable salts and solvates may be formulated for into pharmaceutical compositions for administration by, for example, injection, inhalation or insufflation (either through the mouth or the nose) or oral, buccal, parenteral or rectal administration. In some embodiment, the agent is administered locally, e.g., at the site where the target cells or tissue are present, such as by the use of a patch. Pharmaceutical compositions can be formulated for a variety of loads of administration, including systemic and topical or localized administration. Techniques and formulations generally may be found in *Remmington's Pharmaceutical Sciences*, Meade Publishing Co., Easton, PA. For systemic administration, injection is preferred, including intramuscular, intravenous, intraperitoneal, and subcutaneous. For injection, the compounds can be formulated in liquid solutions, preferably in physiologically compatible buffers such as Hank's solution or Ringer's solution. In addition, the agents may be formulated in solid form and re-dissolved or suspended immediately prior to use. Lyophilized forms are also included.

For oral administration, the pharmaceutical compositions may take the form of, for example, tablets, lozenges, or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound. The pH of the formulations ranges from about 3 to about 11, but is ordinarily about 7 to 10.

Pharmaceutical agents that may oxidize and lose biological activity, especially in a liquid or semisolid form, may be prepared in a nitrogen atmosphere or sealed in a type of capsule and/or foil package that excludes oxygen.

For administration by inhalation, the agents may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin, for use in an inhaler or insufflator may be formulated containing a powder mix of the agent and a suitable powder base such as lactose or starch.

The pharmaceutical agents may be formulated for parenteral administration by injection, e.g., by bolus injection or continuous infusion. Formulations for injection may be presented in unit dosage form, e.g., in ampoules or in multi-dose containers, with an added preservative. The agents may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The pharmaceutical agents may also be formulated in rectal compositions such as suppositories or retention enemas, e.g., containing conventional suppository bases such as cocoa butter or other glycerides.

In addition to the formulations described previously, the agents may also be formulated as a depot preparation. Such long acting formulations may be administered by implantation (for example subcutaneously or intramuscularly) or by intramuscular injection. Thus, for example, the agents may be formulated with suitable polymeric or hydrophobic materials (for example as an emulsion in an acceptable oil) or ion exchange resins, or as sparingly soluble derivatives, for example, as a sparingly soluble salt. Controlled release formula also include patches, e.g., transdermal patches. Patches may be used with a sonic applicator that deploys ultrasound in a unique combination of waveforms to introduce drug molecules through the skin that normally could not be effectively delivered transdermally.

Pharmaceutical compositions (including cosmetic preparations) may comprise from about 0.00001 to 100% such as from 0.001 to 10% or from 0.1% to 5% by weight of one or more agents described herein.

In one embodiment, a pharmaceutical agent described herein, is incorporated into a topical formulation containing a topical earner that is generally suited to topical drug administration and comprising any such material known in the art. The topical carrier may be selected so as to provide the composition in the desired form, e.g., as an ointment, lotion, cream, microemulsion, gel, oil, solution, or the like, and may be comprised of a material of either naturally occurring or synthetic origin. It is preferable that the selected carrier not adversely affect the active agent or other components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like.

Pharmaceutical agents may be incorporated into ointments, which generally are semisolid preparations which are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in Remington's, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid.

Exemplary water-soluble ointment bases are prepared from polyethylene glycols (PEGs) of varying molecular weight; again, reference may be had to Remington's, supra, for further information.

Pharmaceutical agents may be incorporated into lotions, which generally are preparations to be applied to the skin surface without friction, and are typically liquid or semiliquid preparations in which solid particles, including the active agent, are present in a water or alcohol base. Lotions are usually suspensions of solids, and may comprise a liquid oily emulsion of the oil-in-water type. Lotions are preferred formulations for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethylcellulose, or the like. An exemplary lotion formulation for use in conjunction with the present method contains propylene glycol mixed with a hydrophilic petrolatum.

Pharmaceutical agents may be incorporated into creams, which generally are viscous liquid or semisolid emulsions, either oil-in-water or water-in-oil. Cream bases are water-washable, and contain an oil phase, an emulsifier and an aqueous phase. The oil phase is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation, as explained in Remington's, supra, is generally a nonionic, anionic, cationic or amphoteric surfactant.

Pharmaceutical agents may be incorporated into microemulsions, which generally are thermodynamically stable, isotropically clear dispersions of two immiscible liquids, such as oil and water, stabilized by an interfacial film of surfactant molecules (*Encyclopedia of Pharmaceutical Technology* (New York: Marcel Dekker, 1992), volume 9). For the preparation of microemulsions, surfactant (emulsifier), co-surfactant (co-emulsifier), an oil phase and a water phase are necessary. Suitable surfactants include any surfactants that are useful in the preparation of emulsions, e.g., emulsifiers that are typically used in the preparation of creams. The co-surfactant (or "co-emulsifier") is generally selected from the group of poly glycerol derivatives, glycerol derivatives and fatty alcohols. Preferred emulsifier/co-emulsifier combinations are generally although not necessarily selected from the group consisting of: glyceryl monostearate and polyoxyethylene stearate; polyethylene glycol and ethylene glycol palmitostearate; and caprilic and capric triglycerides and oleoyl macrogolglycerides. The water phase includes not only water but also, typically, buffers, glucose, propylene glycol, polyethylene glycols, preferably lower molecular weight polyethylene glycols (e.g., PEG 300 and PEG 400), and/or glycerol, and the like, while the oil phase will generally comprise, for example, fatty acid esters, modified vegetable oils, silicone oils, mixtures of mono- di- and triglycerides, mono- and di-esters of PEG (e.g., oleoyl macrogol glycerides), etc.

Pharmaceutical agents may be incorporated into gel formulations, which generally are semisolid systems consisting of either suspensions made up of small inorganic particles (two-phase systems) or large organic molecules distributed substantially uniformly throughout a carrier liquid (single phase gels). Single phase gels can be made, for example, by combining the active agent, a carrier liquid and a suitable gelling agent such as tragacanth (at 2 to 5%), sodium alginate (at 2-10%), gelatin (at 2-15%), methylcellulose (at 3-5%), sodium carboxymethylcellulose (at 2-5%), carbomer (at 0.3-5%) or polyvinyl alcohol (at 10-20%) together and mixing until a characteristic semisolid product is produced. Other suitable gelling agents include methylhydroxycellulose, polyoxyethylene-polyoxypropylene, hydroxyethylcellulose and gelatin. Although gels commonly employ aqueous carrier liquid, alcohols and oils can be used as the carrier liquid as well.

Various additives, known to those skilled in the art, may be included in formulations, e.g., topical formulations. Examples of additives include, but are not limited to, solubilizers, skin permeation enhancers, opacifiers, preservatives (e.g., anti-oxidants), gelling agents, buffering agents, surfactants (particularly nonionic and amphoteric surfactants), emulsifiers, emollients, thickening agents, stabilizers, humectants, colorants, fragrance, and the like. Inclusion of solubilizers and/or skin permeation enhancers is particularly preferred, along with emulsifiers, emollients and preservatives. An optimum topical formulation comprises approximately: 2 wt. % to 60 wt. %, preferably 2 wt. % to 50 wt. %, solubilizer and/or skin permeation enhancer; 2 wt. % to 50 wt. %, preferably 2 wt. % to 20 wt. %, emulsifiers; 2 wt. % to 20 wt. % emollient; and 0.01 to 0.2 wt. % preservative, with the active agent and carrier (e.g., water) making of the remainder of the formulation. A skin permeation enhancer serves to facilitate passage of therapeutic levels of active agent to pass through a reasonably sized area of unbroken skin. Suitable enhancers are well known in the art and include, for example: lower alkanols such as methanol ethanol and 2-propanol; alkyl methyl sulfoxides such as dimethylsulfoxide (DMSO), decylmethylsulfoxide and tetradecylmethyl sulfboxide; pyrrolidones such as 2-pyrrolidone, N-methyl-2-pyrrolidone and N-(-hydroxyethyl)pyrrolidone; urea; N,N-diethyl-m-toluamide; $C_2$-$C_6$ alkanediols; miscellaneous solvents such as dimethyl formamide (DMF), N,N-dimethylacetamide (DMA) and tetrahydrofurfuryl alcohol; and the 1-substituted azacycloheptan-2-ones, particularly 1-n-dodecylcyclazacycloheptan-2-one (laurocapram; available under the trademark Azone® from Whitby Research Incorporated, Richmond, Va.).

Examples of solubilizers include, but are not limited to, the following: hydrophilic ethers such as diethylene glycol monoethyl ether (ethoxydiglycol) and diethylene glycol monoethyl ether oleate; polyethylene castor oil derivatives such as polyoxy 35 castor oil, polyoxy 40 hydrogenated castor oil, etc.; polyethylene glycol, particularly lower molecular weight polyethylene glycols such as PEG 300 and PEG 400, and polyethylene glycol derivatives such as PEG-8 caprylic/capric glycerides; alkyl methyl sulfoxides such as DMSO; pyrrolidones such as 2-pyrrolidone and N-methyl-2-pyrrolidone; and DMA. Many solubilizers can also act as absorption enhancers. A single solubilizer may be incorporated into the formulation, or a mixture of solubilizers may be incorporated therein.

Suitable emulsifiers and co-emulsifiers include, without limitation, those emulsifiers and co-emulsifiers described with respect to microemulsion formulations. Emollients include, for example, propylene glycol, glycerol, isopropyl myristate, polypropylene glycol-2 (PPG-2) myristyl ether propionate, and the like.

Other active agents may also be included in formulations, e.g., anti-inflammatory agents, analgesics, antimicrobial agents, antifungal agents, antibiotics, vitamins, antioxidants, and sunblock agents commonly found in sunscreen formulations including, but not limited to, anthranilates, benzophenones (particularly benzophenone-3), camphor derivatives, cinnamates (e.g., octyl methoxycinnamate), dibenzoyl methanes (e.g., butyl methoxydibenzoyl methane), p-aminobenzoic acid (PABA) and derivatives thereof, and salicylates (e.g., octyl salicylate).

In certain topical formulations, the active agent is present in an amount in the range of approximately 0.25 wt. % to 75 wt. % of the formulation, preferably in the range of approximately 0.25 wt. % to 30 wt. % of the formulation, more preferably in the range of approximately 0.5 wt. % to 15 wt. % of the formulation, and most preferably in the range of approximately 1.0 wt. % to 10 wt. % of the formulation.

Topical skin treatment compositions can be packaged in a suitable container to suit its viscosity and intended use by the consumer. For example, a lotion or cream can be packaged in a bottle or a roll-ball applicator, or a propellant-driven aerosol device or a container fitted with a pump suitable for finger operation. When the composition is a cream, it can simply be stored in a non-deformable bottle or squeeze container, such as a tube or a lidded jar. The composition may also be included in capsules such as those described in U.S. Pat. No. 5,063,507. Accordingly, also provided are closed containers containing a cosmetically acceptable composition.

In an alternative embodiment, a pharmaceutical formulation is provided for oral or parenteral administration, in which case the formulation may comprise an activating compound-containing microemulsion as described above, and may contain alternative pharmaceutically acceptable carriers, vehicles, additives, etc. particularly suited to oral or parenteral drug administration. Alternatively, an activating compound-containing microemulsion may be administered orally or parenterally substantially as described above, without modification.

Effective dose of a pharmaceutical agent depends at least on the nature of the condition being treated, toxicity, whether the compound is being used prophylactically (lower doses) or against an inflammatory disorder, the method of delivery, and the pharmaceutical formulation, and will be determined by the clinician using conventional dose escalation studies. It can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Administration of an agent may be followed by measuring a factor in the subject, such as measuring the level of NMN, $NAD^+$, NADH, or nicotinamide. In an illustrative embodiment, a biological sample is obtained from a subject following administration of a pharmaceutical agent to the subject, such as by obtaining a biopsy, and the factor is determined in the biopsy. Alternatively, biomarkers, such as plasma biomarkers may be followed. The cell may be any cell of the subject, but in cases in which an agent is administered locally, the cell is preferably a cell that is located in the vicinity of the site of administration. The administration of a compound or composition disclosed herein may increase the level of said factor by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 90%, at least 100%, at least 150%, at least 200%. Other factors that may be monitored include a symptom of aging, weight, body mass, blood glucose sugar levels, blood lipid levels and any other factor that may be measured for monitoring diseases or conditions described herein.

III—THERAPEUTIC METHODS

Provided herein are methods of recovering from, treating, and preventing inflammation, cancer, aging, aging-related disorder, cell death, type II diabetes, radiation damage, radiation exposure, chemotherapy-induced damage, disorders associated with inflammation, cellular senescence, metabolic conditions, mitochondrial dysfunction, among others, improving DNA repair, cell proliferation, cell survival, mitochondrial biogenesis, among others, or increasing the life span of a cell or protect it against certain stresses or apoptosis, among others by providing a compound disclosed herein (e.g., a compound of Formulas I-XIII).

In some embodiments, the compounds and compositions disclosed herein may act to increase the level or activity of nicotinamide dinucleotides (e.g., $NAD^+$, NMN; $NAD^+$ precursor pathways, such as a protein selected from the group consisting of NPT1, PNC1, NMA1 and NMA2; or $NAD^+$ biosynthesis, such as enzymes selected from NMNAT-1, -2, and/or -3 or NAMPT). In some embodiments, the introduction of or treatment with the compounds and compositions disclosed herein blocks the fall of $NAD^+$ levels. In some embodiments, In some embodiments, the introduction of or treatment with the compounds and compositions disclosed herein increases the levels of $NAD^+$. Another aspect of the invention provides a method for treating or preventing a disorder associated with inflammation. In some embodiments, the introduction, treatment, or addition of a compound or compositions disclosed herein mutant/variant may cause inflammation to decrease. In other embodiments, the inflammatory response is depressed or suppressed.

A subject may self-administer the compositions as desired or a physician may administer the compositions. Additionally a physician or other health care worker may select a delivery schedule. In some embodiments, the pharmaceutical compositions are administered on a routine schedule. A routine refers to a predetermined designated period of time. The routine schedule may encompass periods of time which are identical or which differ in length, as long as the schedule is predetermined. For instance, the routine schedule may involve administration of the composition on a daily basis, every two days, every three days, every four days, every five days, every six days, a weekly basis, a monthly basis or any set number of days or weeks there-between, every two months, three months, four months, five months, six months, seven months, eight months, nine months, ten months, eleven months, twelve months, etc. Alternatively, the predetermined routine schedule may involve, for example, administration of the pharmaceutical compositions on a daily basis for the first week, followed by a monthly basis for several months, and then every three months after that. Any particular combination would be covered by the routine schedule as long as it is determined ahead of time that the appropriate schedule involves administration on a certain day. For use in therapy, an effective amount of the pharmaceutical compositions can be administered to a subject by any mode. Administering a pharmaceutical composition of the present invention may be accomplished by any means known to the skilled artisan.

In some embodiments, the invention provides a method extending the life span of a cell, extending the proliferative capacity of a cell, slowing aging of a cell, promoting the survival of a cell, delaying cellular senescence in a cell, mimicking the effects of calorie restriction, increasing the resistance of a cell to stress, or preventing apoptosis of a cell, by contacting the cell with a pharmaceutical composition or compound described herein. Assays for determining the life span of a cell are known in the art. In particular, assays for determining the life span of a mammalian cell can be conducted as described, e.g., in *Cell Growth, Differentiation and Senescence: A Practical Approach*. George P. Studzinski (ed.). Instead of measuring the life span, one can also measure the resistance of a transfected cell to certain stresses, e.g., heatshock. Methods for measuring resistance to certain stresses are known in the art. In particular, assays for determining the resistance of a mammalian cell to heatshock can be conducted as described, e.g., in Bunelli et al. *Exp. Cell Res.* 262: 20 (1999).

In another embodiment, a pharmaceutical composition described herein (e.g. a compound described herein and a pharmaceutically acceptable carrier) that increases the level of intracellular $NAD^+$ may be used for recovering from, treating, or preventing a disease or condition induced or inflammation in a subject; methods for decreasing the inflammatory response in a subject; methods for recovering from, treating or preventing a disease or condition relating to life span (e.g., aging-related disorders); methods for recovering from, treating or preventing a disease or condition relating to the proliferative capacity of cells (e.g., cancer); and methods for recovering from, treating or preventing a disease or condition resulting from cell damage or death (e.g., DNA repair deficiency disorder). For example, the pharmaceutical agents disclosed herein can be used for recovery from mitigation, treatment, or amelioration of a DNA repair deficiency disorder. In certain embodiments, a method does not act by reducing the lethality caused by a disease, such as cancer.

In other embodiments, cells that are intended to be preserved for long periods of time are treated with a compound disclosed herein (e.g., a compound of Formulas I-XIII). The cells can be cells in suspension, e.g., blood cells, serum, biological growth media, or tissues or organs. For example, blood collected from an individual for administering to an individual can be treated as described herein, such as to preserve the blood cells for longer periods of time, such as for forensic purposes. Other cells that one may treat for extending their lifespan or protect against apoptosis include cells for consumption, e.g., cells from non-human mammals (such as meat), or plant cells (such as vegetables).

Generally, compound disclosed herein (e.g., a compound of Formulas I-XIII) may be used for extending the lifespan of a cell; extending the proliferative capacity of a cell; slowing aging of a cell; promoting the survival of a cell; delaying cellular senescence in a cell; or mimicking the effects of calorie restriction (see description below).

In another embodiment, a compound or pharmaceutical composition described herein may be used to treat cells useful for transplantation or cell therapy, including, for example, solid tissue grafts, organ transplants, cell suspensions, stem cells, bone marrow cells, etc. The cells or tissue may be an autograft, an allograft, a syngraft or a xenograft. The cells or tissue may be treated with the pharmaceutical compositions described herein prior to administration/implantation, concurrently with administration/implantation, and/or post administration/implantation into a subject. The cells or tissue may be treated prior to removal of the cells from the donor individual, ex vivo after removal of the cells or tissue from the donor individual, or post implantation into the recipient. For example, the donor or recipient individual may be treated systemically with a pharmaceutical agents described herein (e.g. compositions of Formulas I-XIII) or may have a subset of cells/tissue treated locally with a pharmaceutical agents described herein (e.g. compositions of Formulas I-XIII). In certain embodiments, the cells or tissue (or donor/recipient individuals) may additionally be treated with another therapeutic agent useful for prolonging graft survival, such as, for example, an immunosuppressive agent, a cytokine, an angiogenic factor, etc.

In yet other embodiments, cells may be treated with a pharmaceutical agent described herein (e.g. compositions of Formulas I-XIII) that increases the level of $NAD^+$ in vivo, e.g., to increase their life span or prevent apoptosis. For example, skin can be protected from aging (e.g., developing wrinkles, loss of elasticity, etc.) by treating skin or epithelial cells with a pharmaceutical composition described herein, or cream that increases the level intracellular $NAD^+$. In some embodiments, skin is contacted with a cream, pharmaceutical or cosmetic composition comprising a pharmaceutical agent described herein (e.g. pharmaceutical compositions) that increases the level of intracellular $NAD^+$. Examples of skin afflictions or skin conditions that may be treated in accordance with the methods described herein include disorders or diseases associated with or caused by inflammation, sun damage or natural aging. For example, the compositions described herein find utility for sunburn prevention, recovery from sunburn, and in the prevention or treatment of contact dermatitis (including irritant contact dermatitis and allergic contact dermatitis), atopic dermatitis (also known as allergic eczema), actinic keratosis, keratinization disorders (including eczema), epidermolysis bullosa diseases (including penfigus), exfoliative dermatitis, seborrheic dermatitis, erythemas (including erythema multiforme and erythema nodosum), damage caused by the sun or other light sources, discoid lupus erythematosus, dermatomyositis, psoriasis, skin cancer and the effects of natural aging. In another embodiment, a pharmaceutical composition described herein that increases the level of intracellular $NAD^+$ may be used for the treatment of wounds and/or burns to promote healing, including, for example, first-, second- or third-degree burns and/or thermal, chemical or electrical burns. The formulations may be administered topically, to the skin or mucosal tissue, as an ointment, lotion, cream, microemulsion, gel, solution or the like, as further described herein, within the context of a dosing regimen effective to bring about the desired result.

In some embodiments, characteristics of aging can be obvious. For example, characteristics of older humans include skin wrinkling, graying of the hair, baldness, and cataracts, as well as hypermelanosis, osteoporosis, altered adiposity, cerebral cortical atrophy, lymphoid depletion, memory loss, thymic atrophy, increased incidence of diabetes type II, atherosclerosis, cancer, muscle loss, bone loss, and heart disease. Nehlin et al. *Annals NY Acad Sci* 980: 176-79 (2000). Other aspects of mammalian aging include weight loss, lordokyphosis (hunchback spine), absence of vigor, lymphoid atrophy, decreased bone density, dermal thickening and subcutaneous adipose tissue, decreased ability to tolerate stress (including heat or cold, wounding, anesthesia, and hematopoietic precursor cell ablation), liver pathology, atrophy of intestinal villi, skin ulceration, amyloid deposits, and joint diseases. Tyner et al. Nature 415: 45-53 (2002).

Careful observation reveals characteristics of aging in other eukaryotes, including invertebrates. For example, characteristics of aging in the model organism *C. elegans* include slow movement, flaccidity, yolk accumulation, intestinal autofluorescence (lipofuscin), loss of ability to eat food or dispel waste, necrotic cavities in tissues, and germ cell appearance.

Those skilled in the art will recognize that the aging process is also manifested at the cellular level. Cellular aging is manifested in reduced mitochondrial function, loss of doubling capacity, increased levels of apoptosis, changes in differentiated phenotype, and changes in metabolism, e.g., decreased fatty acid oxidation, respiration, and protein synthesis and turnover.

Given the programmed nature of cellular and organismal aging, it is possible to evaluate the "biological age" of a cell or organism by means of phenotypic characteristics that are correlated with aging. For example, biological age can be deduced from patterns of gene expression, resistance to stress (e.g., oxidative or genotoxic stress), rate of cellular proliferation, and the metabolic characteristics of cells (e.g., rates of protein synthesis and turnover, mitochondrial function, ubiquinone biosynthesis, cholesterol biosynthesis, ATP levels within the cell, levels of a Krebs cycle intermediate in the cell, glucose metabolism, nucleic acid metabolism, ribosomal translation rates, etc.). As used herein, "biological age" is a measure of the age of a cell or organism based upon the molecular characteristics of the cell or organism. Biological age is distinct from "temporal age," which refers to the age of a cell or organism as measured by days, months, and years.

The rate of aging of an organism, e.g., an invertebrate (e.g., a worm or a fly) or a vertebrate (e.g., a rodent, e.g., a mouse) can be determined by a variety of methods, e.g., by one or more of: a) assessing the life span of the cell or the organism; (b) assessing the presence or abundance of a gene transcript or gene product in the cell or organism that has a biological age-dependent expression pattern; (c) evaluating resistance of the cell or organism to stress, e.g., genotoxic stress (e.g., etopocide, UV irradiation, exposure to a mutagen, and so forth) or oxidative stress; (d) evaluating one or more metabolic parameters of the cell or organism; (e) evaluating the proliferative capacity of the cell or a set of cells present in the organism; and (f) evaluating physical appearance or behavior of the cell or organism. In one example, evaluating the rate of aging includes directly measuring the average life span of a group of animals (e.g., a group of genetically matched animals) and comparing the resulting average to the average life span of a control group of animals (e.g., a group of animals that did not receive the test compound but are genetically matched to the group of animals that did receive the test compound). Alternatively, the rate of aging of an organism can be determined by measuring an aging-related parameter.

The pharmaceutical agents described herein (e.g., a compound of Formula I-XIII and compositions comprising a compound of Formula I-XIII) that increases the level of intracellular $NAD^+$ can also be administered to subjects for treatment of diseases, e.g., chronic diseases, associated with cell death, in order to protect the cells from cell death. Exemplary diseases include those associated with neural cell death, neuronal dysfunction, or muscular cell death or dysfunction, such as Parkinson's disease, Alzheimer's disease, multiple sclerosis, amyotrophic lateral sclerosis, and muscular dystrophy; AIDS; fulminant hepatitis; diseases linked to degeneration of the brain, such as Creutzfeldt-Jakob disease, retinitis pigmentosa and cerebellar degeneration; myelodysplasia such as aplastic anemia; ischemic diseases such as myocardial infarction and stroke; hepatic diseases such as alcoholic hepatitis, hepatitis B and hepatitis C; joint-diseases such as osteoarthritis; atherosclerosis; alopecia; damage to the skin due to UV light; lichen planus; atrophy of the skin; cataract; and graft rejections. Cell death can also be caused by surgery, drug therapy, chemical exposure, or radiation exposure.

The compounds and compositions described herein can also be administered to a subject suffering from an acute damage to an organ or tissue, e.g., a subject suffering from stroke or myocardial infarction or a subject suffering from a spinal cord injury or used to repair an alcoholic's liver.

Subjects that may be treated as described herein include eukaryotes, such as mammals, e.g., humans, ovines, bovines, equines, porcines, canines, felines, non-human primate, mice, and rats. Cells that may be treated include eukaryotic cells, e.g., from a subject described above, or plant cells, yeast cells and prokaryotic cells, e.g., bacterial cells.

In some embodiments, a composition can be taken by subjects as a food or dietary supplement. In some embodiments, such a composition is a component of a multi-vitamin complex or as a multi-drug regimen. Compositions can also be added to existing formulations that are taken on a daily basis, e.g., statins and aspirin. Compositions may also be used as food additives. In some embodiments, the multi-drug complex or regimen would include drugs or compositions for the treatment or prevention of aging-related diseases, e.g., stroke, heart disease, arthritis, high blood pressure, Alzheimer's. In some embodiments, this multi-drug regimen would include chemotherapeutic drugs for the treatment of cancer. In some embodiments, a composition could be used to protect non-cancerous cells from the effects of chemotherapy or for recovering from, treating, or preventing chemotherapy-induced damage.

The compositions and compounds described herein may also be applied during developmental and growth phases in mammals, plants, insects or microorganisms, in order to, e.g., alter, retard or accelerate the developmental and/or growth process.

In other embodiments, cells obtained from a subject, e.g., a human or other mammal, are treated according to methods described herein and then administered to the same or a different subject. Accordingly, cells or tissues obtained from a donor for use as a graft can be treated as described herein prior to administering to the recipient of the graft. For example, bone marrow cells can be obtained from a subject, treated ex vivo, e.g., to extend their lifespan, and then administered to a recipient. The graft can be an organ, a tissue or loose cells.

In yet other embodiments, cells are treated in vivo, e.g., to increase their lifespan or prevent apoptosis. For example, skin can be protected from aging, e.g., developing wrinkles, by treating skin, e.g., epithelial cells, as described herein.

Topical formulations described above may also be used as preventive, e.g., chemopreventive, compositions. When used in a chemopreventive method, susceptible skin is treated prior to any visible condition in a particular individual.

In one embodiment, cells are treated in vitro to mimic caloric restriction, such as to extend their lifespan, e.g., to keep them proliferating longer and/or increasing their resistance to stress or prevent apoptosis.

Compounds can also be delivered locally, e.g., to a tissue or organ within a subject, such as by injection, e.g., to extend the lifespan of the cells; protect against apoptosis or induce apoptosis.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual* 2$^{nd}$ Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986);
B. Perbal, *A Practical Guide To Molecular Cloning* (1984); the treatise, Methods In Enzymology (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); *Manipulating the Mouse Embryo*, (Cold Spring Harbor Laboratory Press, Cold Spring Harbor, N.Y., 1986).

In some embodiments, the compounds and compositions disclosed herein are administered conjointly with a sirtuin-activating compound. A sirtuin activating compound may include any compound that increases or activates SIRT1 activity. Sirtuin activating compounds include, but are not limited to, polyphenols, such as resveratrol, butein, piceatannol, isoliquiritigenin, fisetin, and quercetin. In certain embodiments, agents of the invention may be used alone or conjointly administered with another type of therapeutic agent. As used herein, the phrase "conjoint administration" refers to any form of administration of two or more different therapeutic agents such that the second agent is administered while the previously administered therapeutic agent is still effective in the body (e.g., the two agents are simultaneously effective in the subject, which may include synergistic effects of the two agents). For example, the different therapeutic agents can be administered either in the same formulation or in separate formulations, either concomitantly or sequentially. In certain embodiments, the different therapeutic agents can be administered within about one hour, about 12 hours, about 24 hours, about 36 hours, about 48 hours, about 72 hours, or about a week of one another. Thus, a subject who receives such treatment can benefit from a combined effect of different therapeutic agents.

The selected dosage level will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician having ordinary skill in the art can readily determine and prescribe the effective amount of the pharmaceutical composition required. For example, the physician could prescribe and/or administer doses of the compounds employed in the pharmaceutical composition at levels lower than that required in order to achieve the desired therapeutic effect and gradually increase the dosage until the desired effect is achieved.

IV—DEFINITIONS

The articles "a" and "a" are used herein to refer to one or to more than one (i.e. to at least one) of the grammatical object of the article. By way of example, "an element" means one element or more than one element.

The term "acyl" is art-recognized and refers to a group represented by the general formula hydrocarbylC(O)—, preferably alkylC(O)— or heteroalkylC(O)—.

The term "acylamino" is art-recognized and refers to an amino group substituted with an acyl group and may be represented, for example, by the formula hydrocarbylC(O) NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, —OCF$_3$, ethoxy, propoxy, tert-butoxy and the like.

The term "cycloalkyloxy" refers to a cycloakyl group having an oxygen attached thereto.

The term "alkoxyalkyl" refers to an alkyl group substituted with an alkoxy group and may be represented by the general formula alkyl-O-alkyl.

The term "alkylaminoalkyl" refers to an alkyl group substituted with an alkylamino group.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Typically, an alkenyl has from 1 to about 20 carbon atoms, from about 1 to 15 carbon atoms, or from 1 to about 10 unless otherwise defined. Substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, from about 1 to 15 carbon atoms, or from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A C$_1$-C$_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Exemplary substituted alkyls are described below. Cycloalkyls can be further substituted with alkyls, alkenyls, alkoxys, alkylthios, aminoalkyls, carbonyl-substituted alkyls, —CF$_3$, —CN, and the like.

The term "C$_{x-y}$" when used in conjunction with a chemical moiety, such as acyl, acyloxy, alkyl, alkenyl, alkynyl, or alkoxy is meant to include groups that contain from x to y carbons in the chain. For example, the term "C$_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2, 2-trifluoroethyl, etc. C$_0$ alkyl indicates a hydrogen where the group is in a terminal position, a bond if internal. The terms "C$_{2-y}$alkenyl" and "C$_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

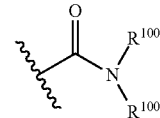

wherein each R$^{100}$ independently represent a hydrogen or hydrocarbyl group, or two R$^{100}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

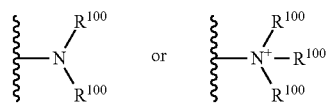

wherein each R$^{100}$ independently represents a hydrogen or a hydrocarbyl group, or two R$^{100}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

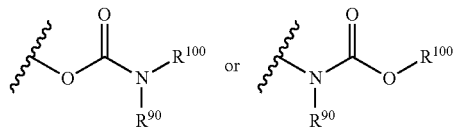

wherein $R^{90}$ and $R^{100}$ independently represent hydrogen or a hydrocarbyl group, such as an alkyl group, or $R^{90}$ and $R^{100}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0] octane, 4,5,6,7-tetrahydro-1H-indene and bicyclo[4.1.0] hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —OCO$_2$—R$^{10}$, wherein R$^{10}$ represents a hydrocarbyl group.

The term "carboxy", as used herein, refers to a group represented by the formula —CO$_2$H.

The term "ester", as used herein, refers to a group —C(O)OR$^{10}$ wherein R$^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical.

Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The term "heteroalkylamino", as used herein, refers to an amino group substituted with a heteralkyl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, benzimidazole, quinoline, isoquinoline, quinoxaline, quinazoline, indole, isoindole, indazole, benzoxazole, pyrazine, pyridazine, purine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like. Heterocyclyl groups can also be substituted by oxo groups. For example, "heterocyclyl" encompasses both pyrrolidine and pyrrolidinone.

The term "heterocycloalkyl", as used herein, refers to an alkyl group substituted with a heterocycle group.

The term "heterocycloalkylamino", as used herein refers to an amino group substituted with a heterocycloalkyl group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

As used herein, the term "oxo" refers to a carbonyl group. When an oxo substituent occurs on an otherwise saturated group, such as with an oxo-substituted cycloalkyl group (e.g., 3-oxo-cyclobutyl), the substituted group is still intended to be a saturated group. When a group is referred to as being substituted by an "oxo" group, this can mean that a carbonyl moiety (i.e., —C(=O)—) replaces a methylene unit (i.e., —CH$_2$—).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the poly cycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

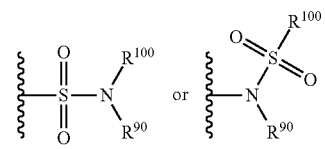

wherein R$^{90}$ and R$^{100}$ independently represents hydrogen or hydrocarbyl, such as alkyl, or R$^{90}$ and R$^{100}$ taken together with the intervening atom(s) complete a heterocycle having from 4 to 8 atoms in the ring structure.

The term "sulfoxide" is art-recognized and refers to the group —S(O)—R$^{100}$, wherein R$^{100}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^{100}$, wherein R$^{100}$ represents a hydrocarbyl.

The term "thioalkyl", as used herein, refers to an alkyl group substituted with a thiol group.

The term "thioester", as used herein, refers to a group —C(O)SR$^{100}$ or —SC(O)R$^{100}$ wherein R$^{100}$ represents a hydrocarbyl.

The term "thioether", as used herein, is equivalent to an ether, wherein the oxygen is replaced with a sulfur.

The term "urea" is art-recognized and may be represented by the general formula

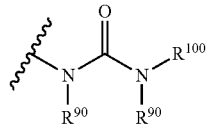

wherein R$^{90}$ and R$^{100}$ independently represent hydrogen or a hydrocarbyl, such as alkyl, or either occurrence of R$^{90}$ taken together with R$^{100}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxylprotecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

As used herein, "aging-related disorders", include but not limited to, Alzheimer's disease, diabetes mellitus, heart disease, obesity, osteoporosis, Parkinson's disease, stroke, amniotropic lateral sclerosis, arthritis, atherosclerosis, cachexia, cancer, cardiac hypertrophy, cardiac failure, cardiac hypertrophy, cardiovascular disease, cataracts, colitis, chronic obstructive pulmonary disease, dementia, diabetes mellitus, frailty, heart disease, hepatic steatosis, high blood cholesterol, high blood pressure, Huntington's disease, hyperglycemia, hypertension, infertility, inflammatory bowel disease, insulin resistance disorder, lethargy, metabolic syndrome, muscular dystrophy, multiple sclerosis, neuropathy, nephropathy, obesity, osteoporosis, Parkinson's disease, psoriasis, retinal degeneration, sarcopenia, sleep disorders, sepsis, and/or stroke.

As used herein, the term "increased" and grammatical equivalents thereof refer to a level, amount, concentration of a parameter, such as a chemical compound, a metabolite, a nucleic acid, a polypeptide, a physical parameter (pH, temperature, viscosity, etc.), or a microorganism measured in a sample that has an increase of at least 30%, preferably about 50%, more preferable about 75%, and still more preferably an increase of more than 100% when compared to the level, amount, or concentration of the same chemical compound, nucleic acid, polypeptide, physical parameter, or microorganism in a control sample. In some embodiments, the term describes the levels of NAD$^+$. In some embodiments, the parameter is detectable in a subject sample, while it is not detectable in a control sample.

As used herein an "inflammatory disorder" is a condition or disease associated with inflammation, including but not limited to, septic shock, obesity-related inflammation, Parkinson's Disease, Crohn's Disease, Alzheimer's Disease, cardiovascular disease, inflammatory bowel disease, chronic obstructive pulmonary disease, an allergic reaction, an autoimmune disease, blood inflammation, joint inflammation, arthritis, asthma, ulcerative colitis, hepatitis (e.g., viral chronic hepatitis), psoriasis, atopic dermatitis, pemphigus, glomerulonephritis, atherosclerosis, sarcoidosis, rheumatoid arthritis, psoriatic arthritis, ankylosing spondylitis, Wegner's syndrome, Goodpasture's syndrome, giant cell arteritis, polyarteritis nodosa, idiopathic pulmonary fibrosis, acute lung injury, post-influenza pneumonia, SARS, tuberculosis, malaria, sepsis, cerebral malaria, Chagas disease, schistosomiasis, bacterial and viral meningitis, cystic fibrosis, multiple sclerosis, encephalomyelitis, sickle cell anemia, pancreatitis, transplantation (e.g., host-mediated rejection of transplanted tissue such as hematopoietic stem cells or an organ, graft mediated host response, such as graft vs. host disease), systemic lupus erythematosus, autoimmune diabetes, thyroiditis, radiation pneumonitis, respiratory inflammation and pulmonary inflammation.

As used herein, nicotinamide adenine dinucleotide or "NAD$^+$" and its derivative compounds are known as essential coenzymes in cellular redox reactions in all living organisms. Several lines of evidence have also shown that NAD participates in a number of important signaling pathways in mammalian cells, including poly(ADP-ribosyl)ation in DNA repair (Menissier de Murcia et al. *EMBO J.* 22:2255-2263 (2003)), mono-ADP-ribosylation in the immune response and G protein-coupled signaling (Corda et al. *EMBO J.* 22:1953-8 (2003)), and the synthesis of cyclic ADP-ribose and nicotinate adenine dinucleotide phosphate (NAADP) in intracellular calcium signaling (Lee, *Annu. Rev. Pharmacol. Toxicol.*, 41:317-345 (2001)). It has also been shown that NAD and its derivatives play an important role in transcriptional regulation (Lin et al. *Curr. Opin. Cell. Biol* 15:241-246 (2003); Imai et al. *Nature* 403:795-800 (2000); Landry et al. *Biochem. Biophys. Res. Commun.* 278:685-690 (2000); Smith et al. Proc. *Natl. Acad Set. USA* 97:6658-6663 (2000)).

The NAD biosynthesis pathways have been characterized in prokaryotes by using *Escherichia coli* and *Salmonella typhimurium* (Penfound et al. *Cellular and Molecular Biology*, p. 721-730, ed. Neidhardt, F. C., 1996, ASM Press: Washington, D.C.) and in yeast (Lin et al. *Curr. Opin. Cell. Biol.* 15:241-246 (2003); Denu *Trends Biochem. Sci.*, 28:41-48 (2003)). In prokaryotes and lower eukaryotes, NAD is synthesized by the de novo pathway via quinolinic acid and by the salvage pathway via nicotinic acid (Penfound, Id). In yeast, the de novo pathway begins with tryptophan, which is converted to nicotinic acid mononucleotide (NaMN) through six enzymatic steps and one non-enzymatic reaction (Lin et al. *Curr. Opin. Cell. Biol.* 15:241-246 (2003)).

In mammals, NAD$^+$ is generated from nicotinamide in a salvage pathway wherein nicotinamide phosphoribosyltransferase (NAMPT) converts nicotinamide to nicotinamide mononucleotide (NMN) which is then converted to NAD$^+$ by nicotinamide mononucleotide adenylyltransferase (NMNAT) (Canto et al. *Cold Spring Harbor symposia on quantitative biology* 76, 291-298 (2011)).

The phrase "pharmaceutically-acceptable carrier" as used herein means a pharmaceutically-acceptable material, composition or vehicle, such as a liquid or solid filler, diluent, excipient, or solvent encapsulating material, which may be involved in carrying or transporting the subject compound from one organ, or portion of the body, to another organ, or portion of the body.

The terms "prevent," "preventing," "prevention," and the like refer to reducing the probability of developing a disease, disorder, or condition in a subject, who does not have, but is at risk of or susceptible to developing a disease, disorder, or condition.

As used herein, the term "subject" means a human or non-human animal selected for treatment or therapy.

As used herein, the terms "effective amount," "effective dose," "sufficient amount," "amount effective to," "therapeutically effective amount," or grammatical equivalents thereof mean a dosage sufficient to produce a desired result, to ameliorate, or in some manner, reduce a symptom or stop or reverse progression of a condition and provide either a subjective relief of a symptom(s) or an objectively identifiable improvement as noted by a clinician or other qualified observer. Amelioration of a symptom of a particular condition by administration of a pharmaceutical composition or compound described herein refers to any lessening, whether permanent or temporary, lasting or transit that can be associated with the administration of the pharmaceutical composition. With respect to "effective amount," "effective dose," "sufficient amount," "amount effective to," or "therapeutically effective amount" of a pharmaceutical composition, the dosing range varies with the pharmaceutical composition used, the route of administration and the potency of the particular pharmaceutical composition.

"Treating" a disease in a subject or "treating" a subject having a disease refers to subjecting the subject to a pharmaceutical treatment, e.g., the administration of a drug, such that at least one symptom of the disease is decreased or prevented from worsening.

V—EXAMPLES

Examples of compounds disclosed herein (e.g., of Formula I-XIII) or pharmaceutically acceptable salts thereof having useful biological activity are listed above in Table 1 and Table 2.

Example 1: Chemical Syntheses

The general procedures used in the methods to prepare the compounds of the present invention are detailed in Schemes 1-3.

Synthetic Scheme 1
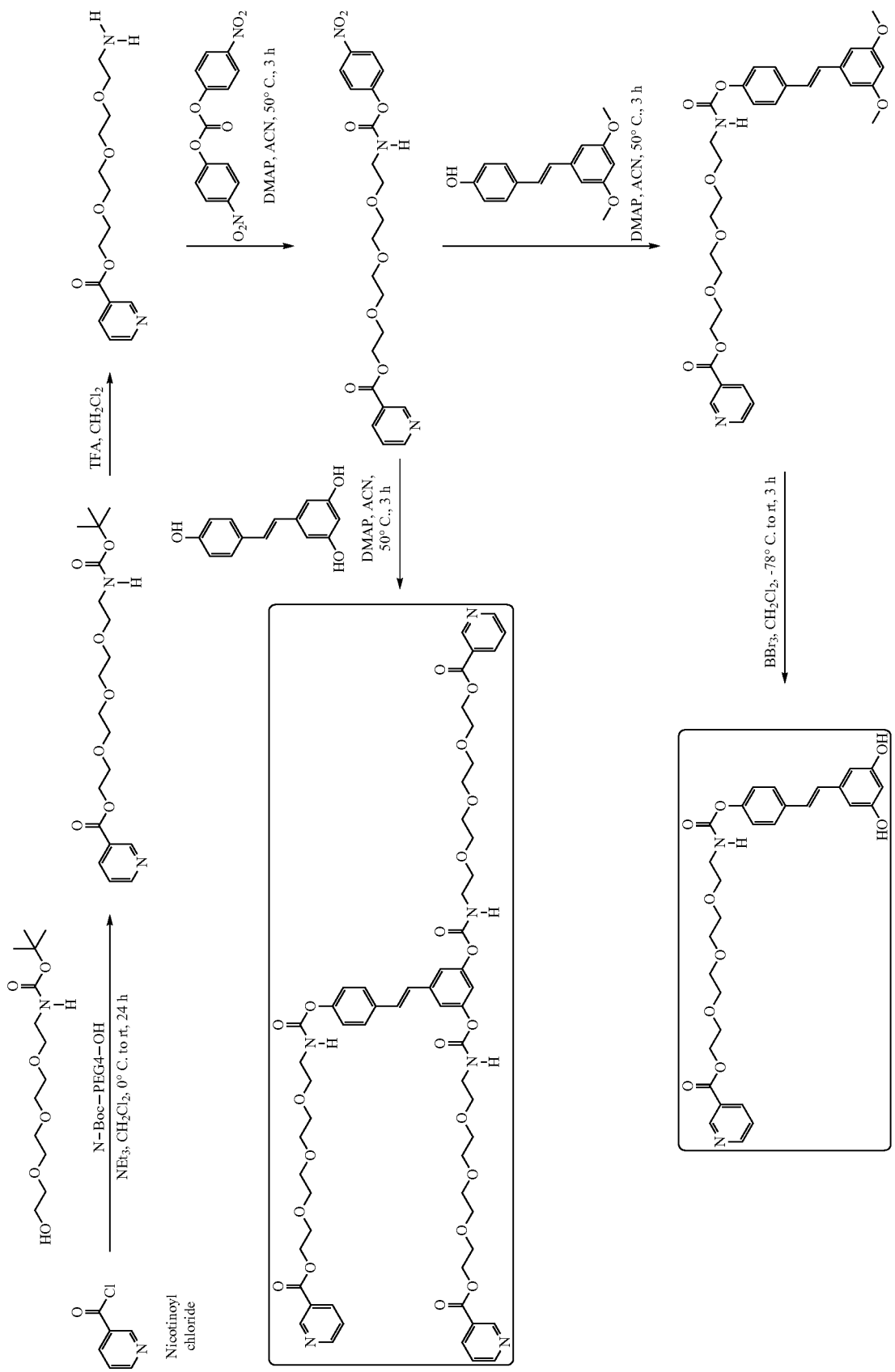

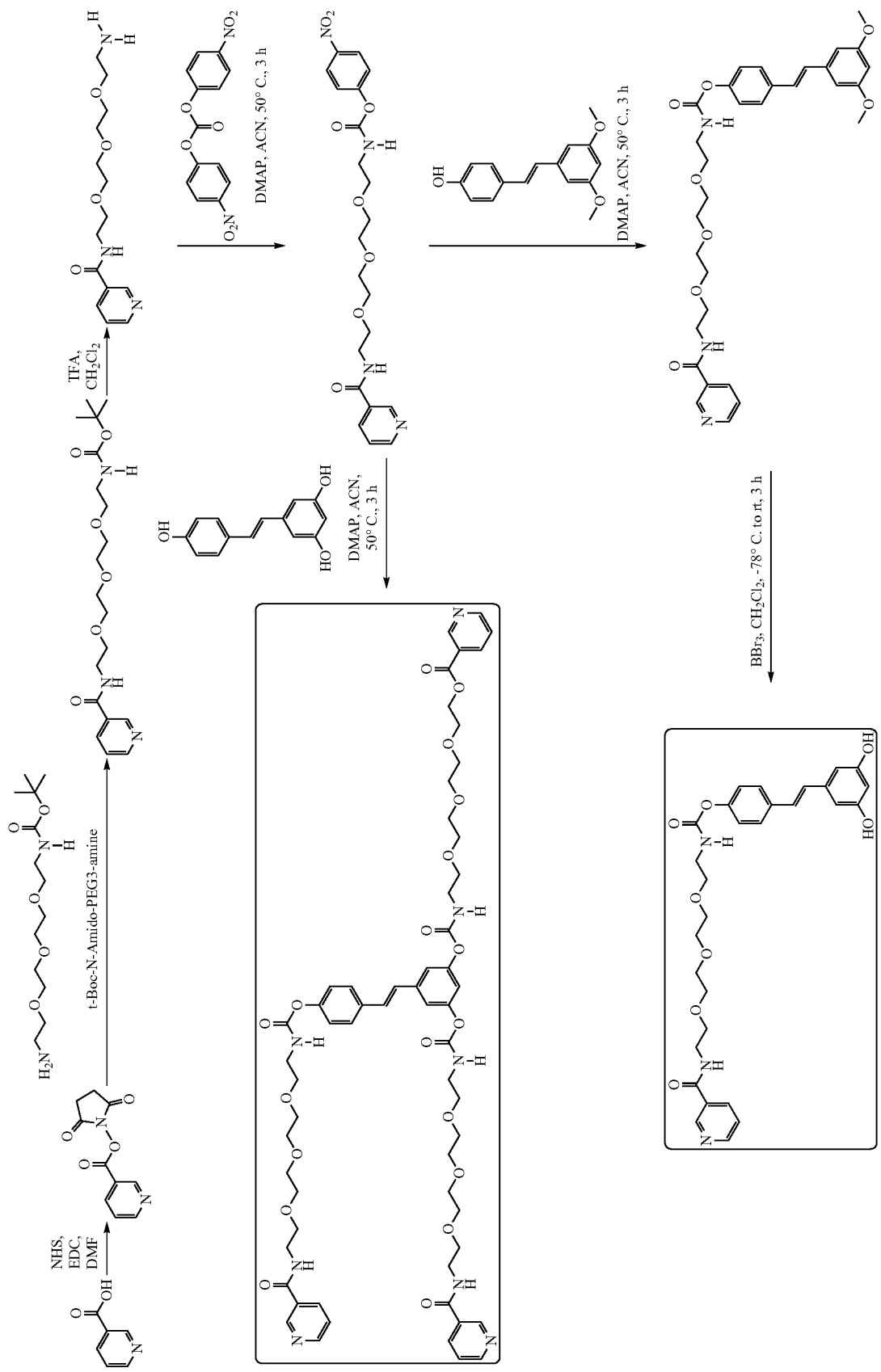

Synthetic Scheme 3

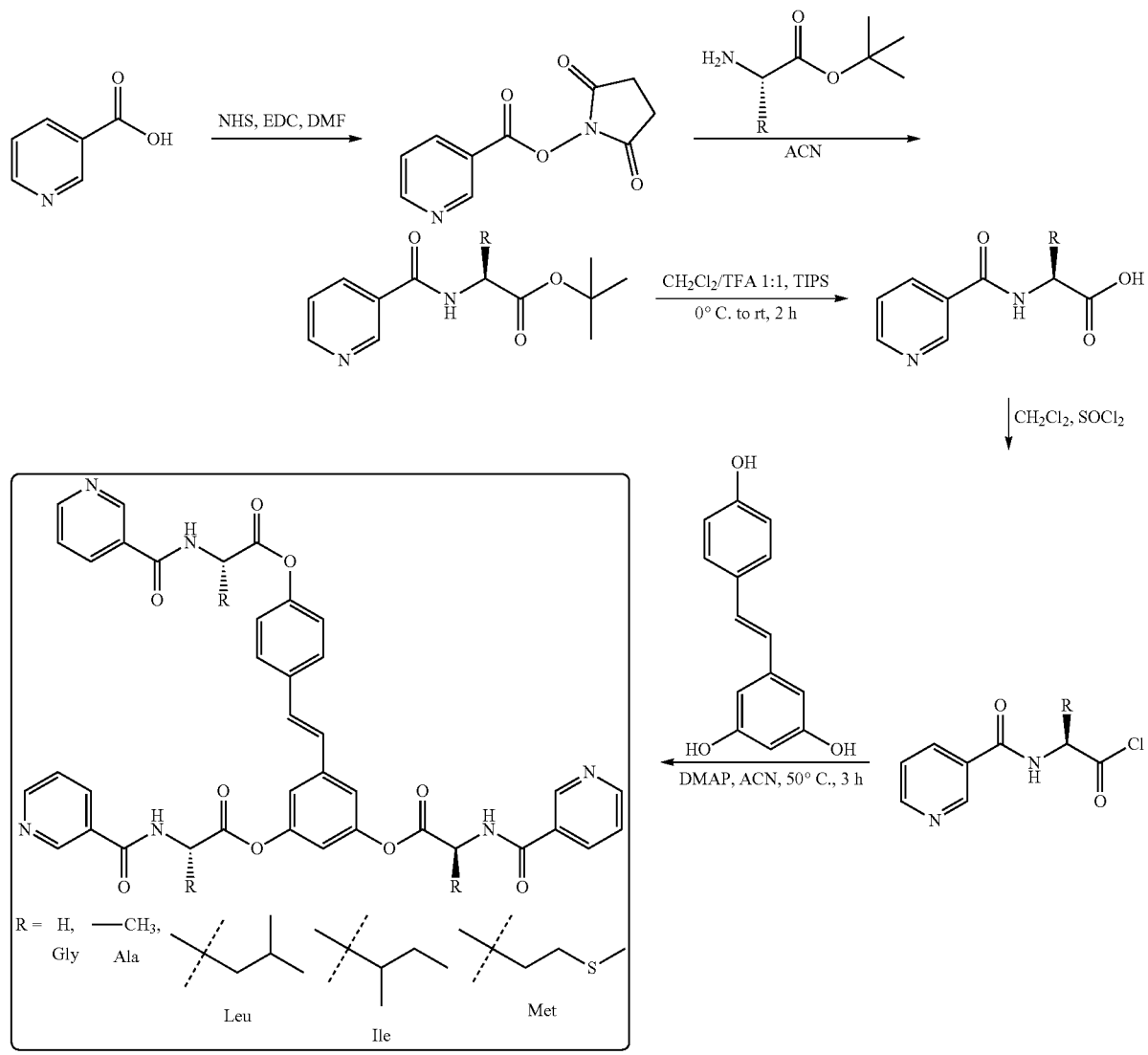

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the World Wide Web and/or the National Center for Biotechnology Information (NCBI) on the World Wide Web.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A compound having a structure of Formula I, II or III, or a pharmaceutically acceptable salt thereof:

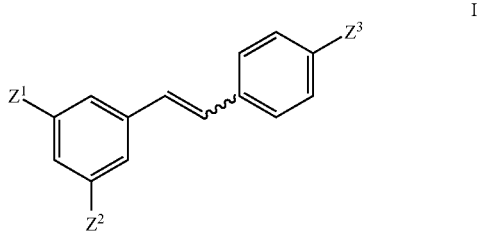

-continued

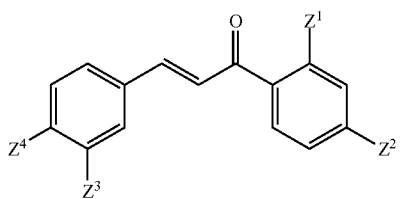
II

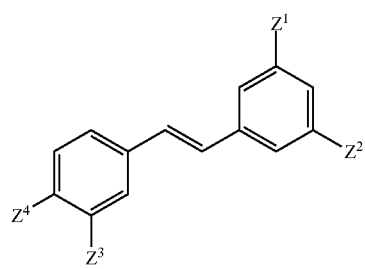
III wherein $Z^1$, $Z^2$, $Z^3$, and $Z^4$ are each independently selected from —OC(O)-$L^1$-$R^1$, —OC($NR^6$)-$L^1$-$R^1$, and

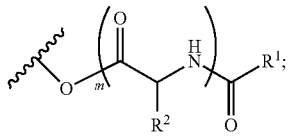

if the compound has the structure of Formula I, $L^1$ is a linker group selected from

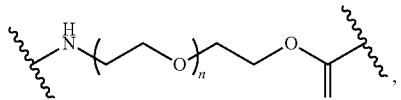

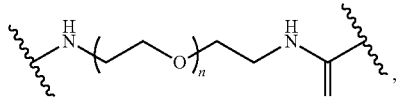

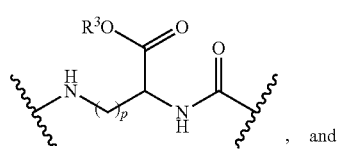
, and

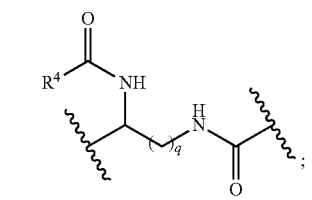
;

if the compound has the structure of Formula II or III, L' is absent or a linker group selected from

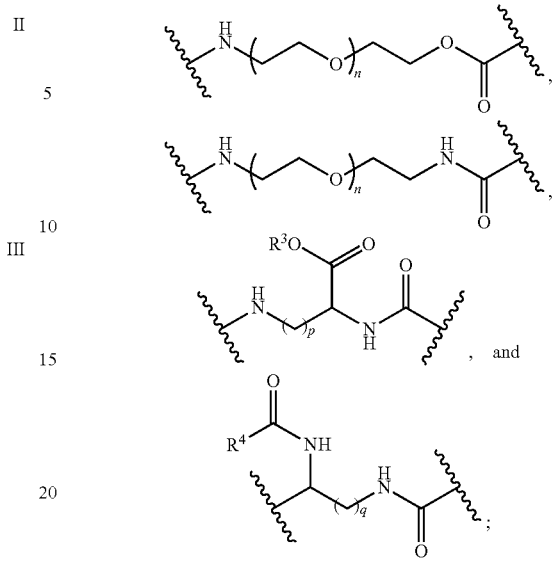

$R^1$ is

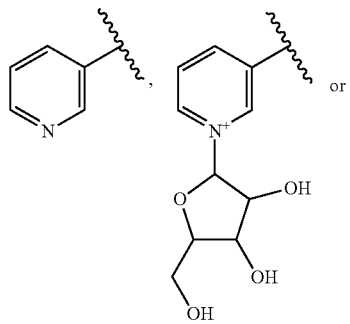

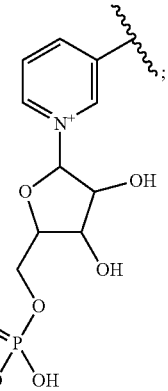
;

$R^2$ is independently selected from H, optionally substituted alkyl, heteroalkyl, aralkyl, and heteroaralkyl;

$R^3$ is selected from H, optionally substituted alkyl, heteroalkyl, aryl, and heteroaryl;

$R^4$ is selected from H, optionally substituted alkyl, heteroalkyl, alkenyl, aryl, and heteroaryl;

$R^6$ is selected from H and alkyl; and m, n, p, q are each independently an integer selected from 1 to 10.

2. The compound of claim 1, wherein the compound has the structure of Formula Ia or a pharmaceutically acceptable salt thereof:

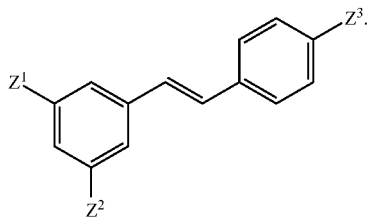
Ia

3. The compound of claim 1, wherein the compound has the structure of Formula Ib or a pharmaceutically acceptable salt thereof:

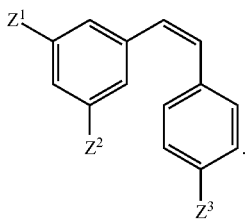
Ib

4. The compound of claim 1, wherein $Z^1=Z^2=Z^3$.
5. The compound of claim 1, wherein $Z^1=Z^{2=73}=Z^4$.
6. The compound of claim 1, wherein $R^1$ is

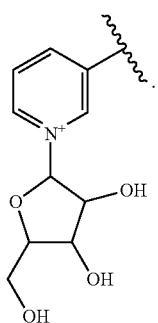 [SMILES: *c1ccc[n+](C2OC(CO)C(O)C2O)c1]

7. The compound of claim 1, wherein n is selected from 3, 4, 5, and 6.
8. The compound of claim 1, wherein $R^4$ is straight chained alkyl group having 10 to 20 carbon atoms.
9. The compound of claim 8, wherein $R^4$ is

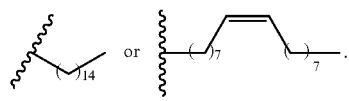

10. The compound of claim 1, wherein q is 3, 4, or 5.
11. The compound of claim 1, wherein each $R^2$ is independently selected from H,

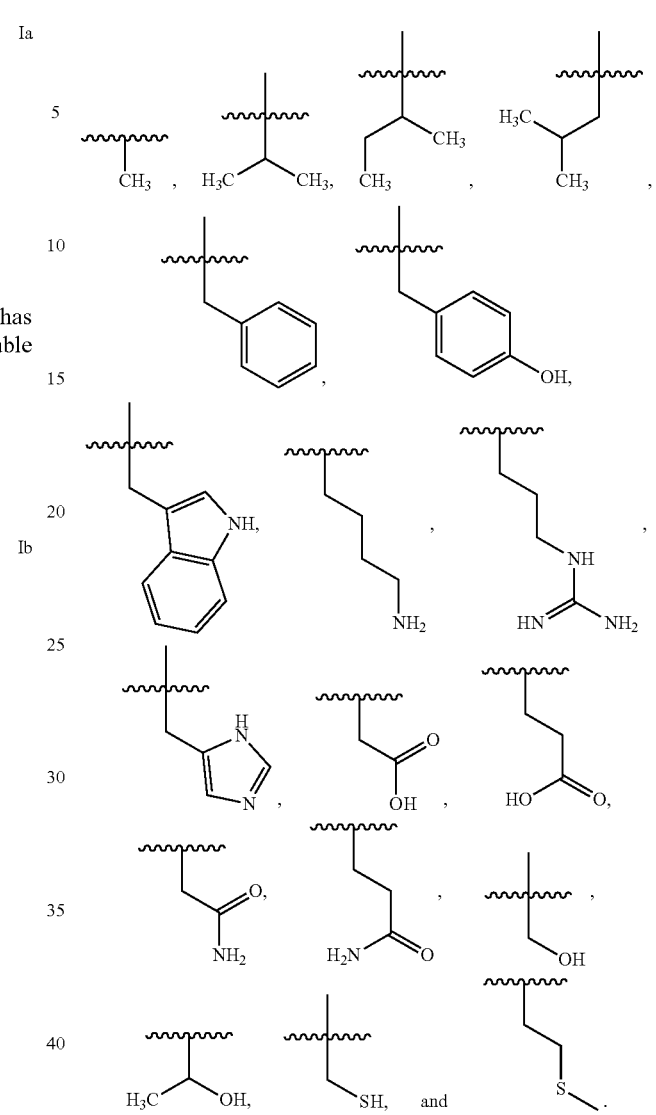

12. The compound of claim 11, wherein $R^2$ is selected from H,

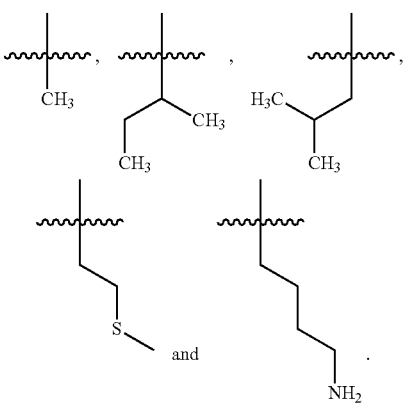

13. The compound of claim 1, wherein $Z^1$, $Z^2$, and $Z^3$ are each independently selected from

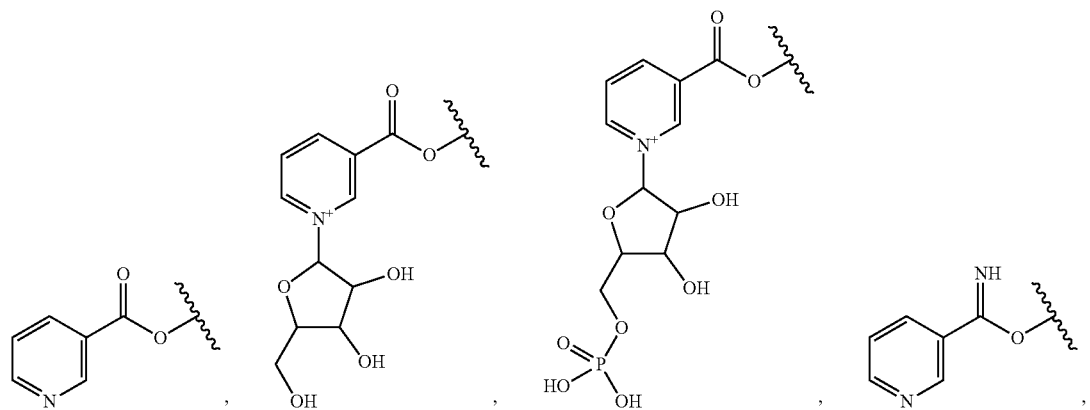
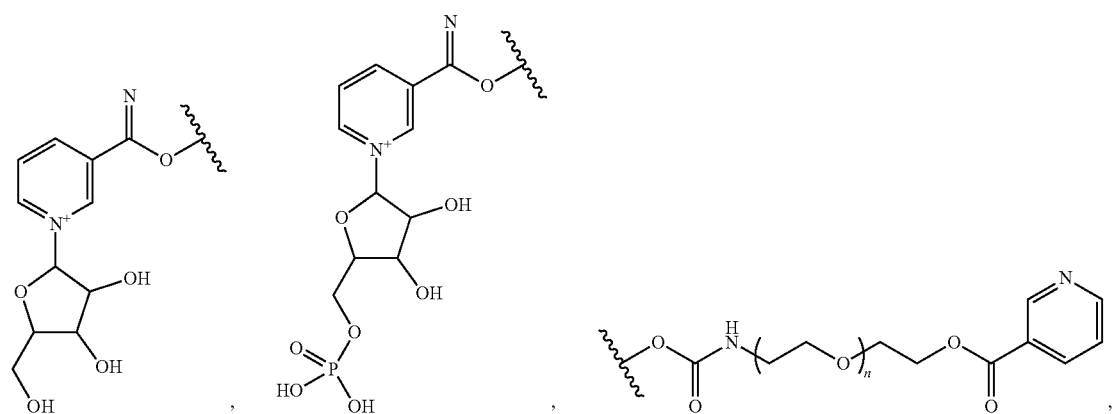
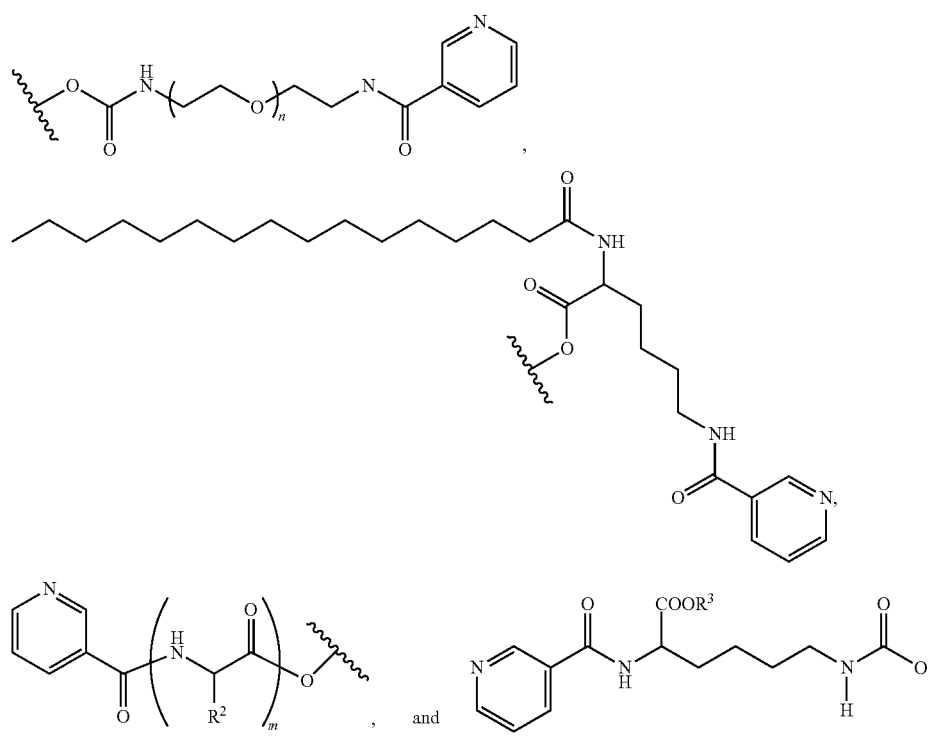

14. The compound of claim 1, wherein the compound is:
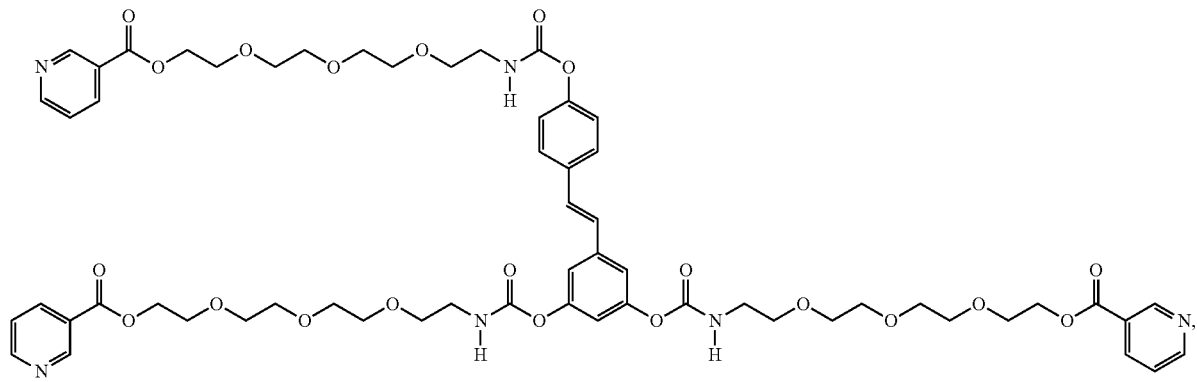
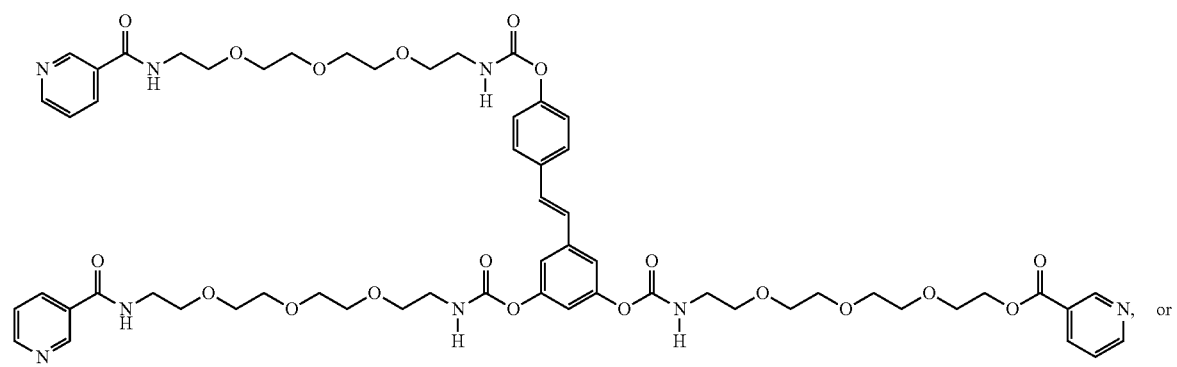
or
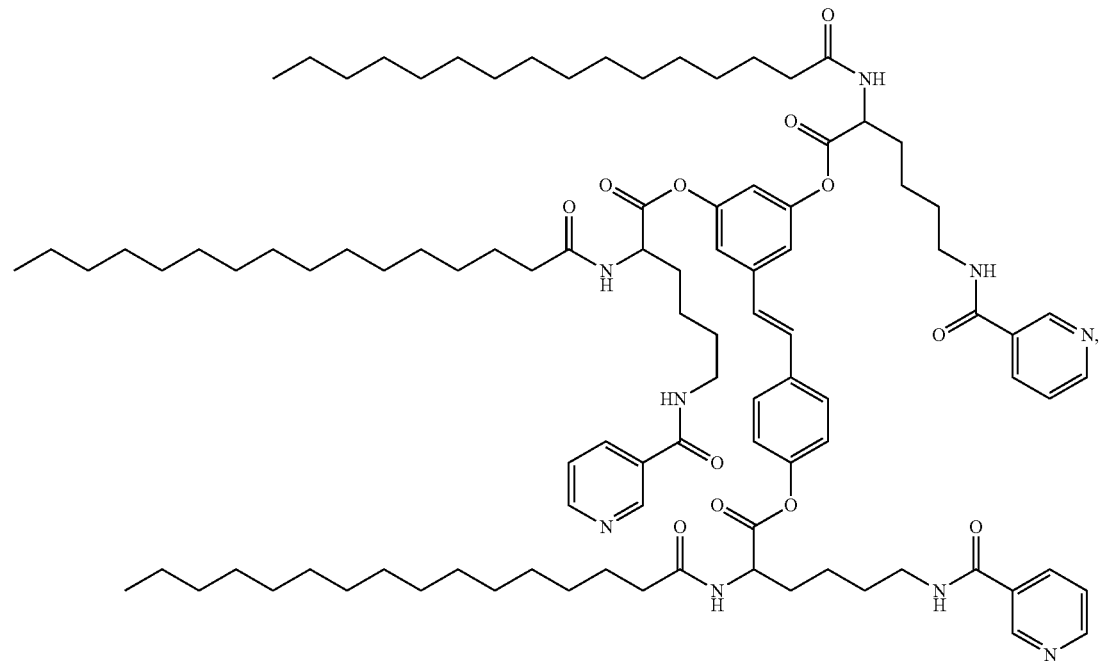
or a pharmaceutically acceptable salt thereof.

15. The compound of claim 1, wherein the compound has the structure of Formula II or III.

16. The compound of claim 15, wherein the compound is

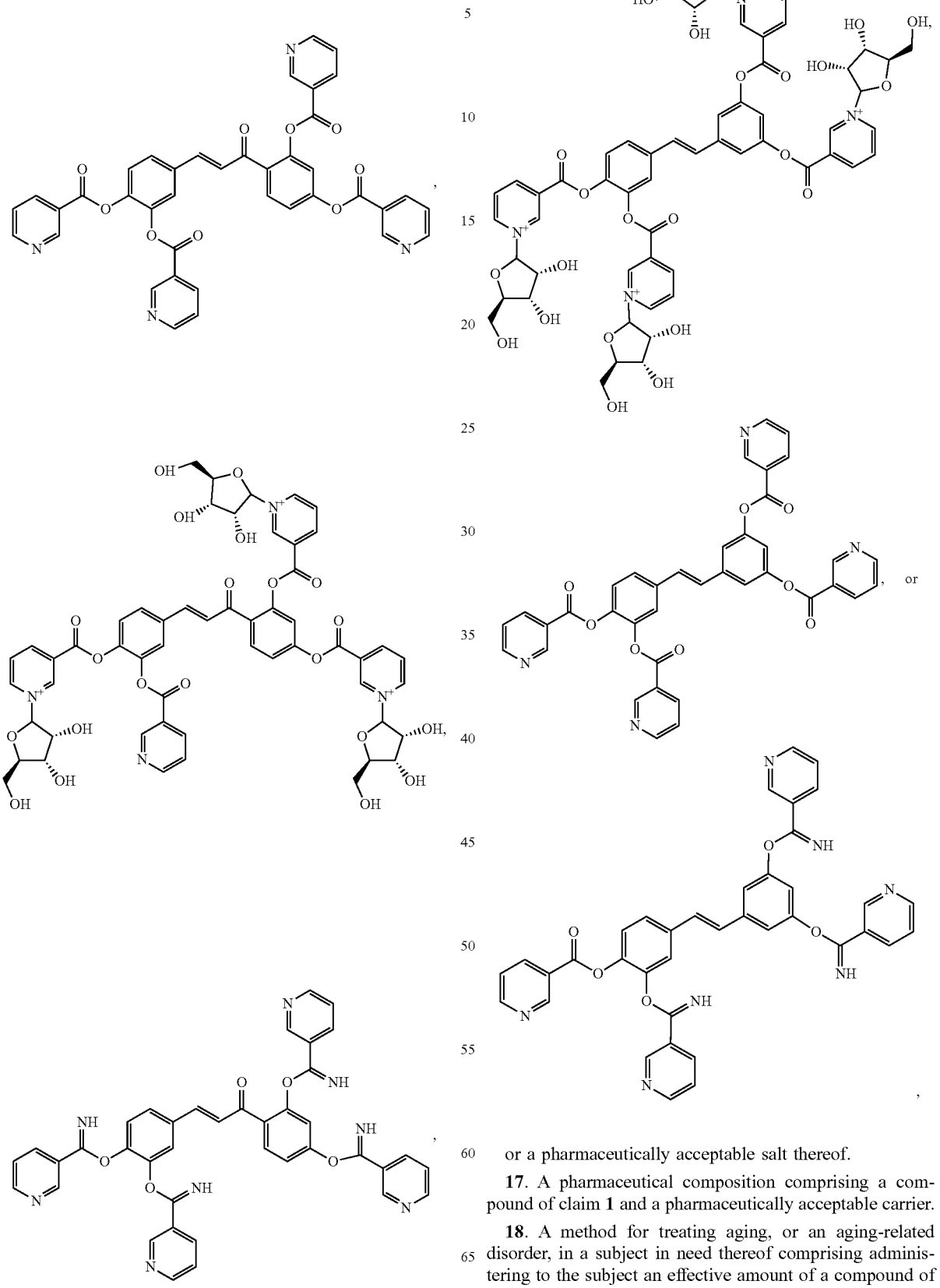

or a pharmaceutically acceptable salt thereof.

17. A pharmaceutical composition comprising a compound of claim 1 and a pharmaceutically acceptable carrier.

18. A method for treating aging, or an aging-related disorder, in a subject in need thereof comprising administering to the subject an effective amount of a compound of claim 1.

19. A method for treating a disorder associated with inflammation in a subject in need thereof comprising administering to the subject an effective amount a compound of claim 1.

* * * * *